(12) United States Patent
Naheed

(10) Patent No.: US 9,827,322 B2
(45) Date of Patent: Nov. 28, 2017

(54) MEDICATION DISPENSING SYSTEM

(71) Applicant: Shabana Naheed, San Jose, CA (US)

(72) Inventor: Shabana Naheed, San Jose, CA (US)

(73) Assignee: Bao Tran, Saratoga, CA (US)

( * ) Notice: Subject to any disclaimer, the term of this patent is extended or adjusted under 35 U.S.C. 154(b) by 292 days.

(21) Appl. No.: 14/808,310

(22) Filed: Jul. 24, 2015

(65) Prior Publication Data

US 2017/0021026 A1    Jan. 26, 2017

(51) Int. Cl.
| | |
|---|---|
| *A01N 65/00* | (2009.01) |
| *A61K 47/36* | (2006.01) |
| *A61K 36/185* | (2006.01) |
| *A61K 9/00* | (2006.01) |
| *A61M 37/00* | (2006.01) |
| *A61K 47/44* | (2017.01) |

(52) U.S. Cl.
CPC ............ *A61K 47/36* (2013.01); *A61K 9/0021* (2013.01); *A61K 36/185* (2013.01); *A61K 47/44* (2013.01); *A61M 37/0015* (2013.01); *A61M 2037/0023* (2013.01); *A61M 2037/0061* (2013.01)

(58) Field of Classification Search
CPC ...................................................... A61K 36/00
USPC ........................................................ 424/725
See application file for complete search history.

(56) References Cited

FOREIGN PATENT DOCUMENTS

CN        101590130 A    * 12/2009

* cited by examiner

*Primary Examiner* — Michael Meller
(74) *Attorney, Agent, or Firm* — Tran & Associates

(57) ABSTRACT

A method for treating cancer is disclosed by boiling blended *cannabis* material with oil and collecting oil infused with *cannabis*; targeting cancerous cells in a body; and injecting the oil infused with *cannabis* into the body portion with cancerous cells.

1 Claim, 3 Drawing Sheets

MEDICATION DISPENSING SYSTEM

FIELD OF THE INVENTION

This invention relates to medical dispensers.

BACKGROUND OF THE INVENTION

*Cannabis* is a substance derived from the hemp plant (*Cannabis indica* or *Cannabis sativa*); the leaves and stalks of these plants may be referred to as hashish or marijuana. The term *cannabis* may refer to the female flowering heads of hemp, or to a resin obtained from the flowering heads that may also be referred to as cannabin. Derived materials include cannaboid, an alkaloid cannabine, and an oil cannabinol. In this specification these, and other derivatives, are referred to generically as *cannabis*.

SUMMARY

A delivery system is disclosed. The delivery system includes transdermal patches, aerosol sprays, or injectable needles/cannulas. In one embodiment, the injectable needles/cannulas are 3D printed hyaluronic acid structures that are hard structures prior to use and when in use, the hyaluronic acid expands upon contact with liquid and create a delivery pathway.

In a second aspect, the transdermal patches have a plurality of needles made from hyaluronic acid (HA). In a first state, the HA is a solid that can penetrate the skin. In a second state, with liquid, the HA becomes expanded to release drug/medication into the skin penetration to deliver drug or solution.

In another aspect, a slow release system using HA and a drug is disclosed. The HA is cross-linked to provide predetermined dissolution to release the medication in different layers of HA for release over time.

In another aspect, CBD can be delivered by mixing blended *cannabis* material with hyaluronic acid (HA); identifying cancerous cells in a body; and contacting the HA infused with *cannabis* into the body portion with cancerous cells.

In another aspect, CBD can be delivered by encapsulating *cannabis* material with hyaluronic acid (HA); cross-linking the HA to provide a slow release *cannabis*; identifying cancerous cells in a body; and contacting the HA infused with *cannabis* into the body portion with cancerous cells for time release. Cannabinoid are hydrophobic while HA is hydrophilic so the HA can bind to body better than *cannabis* alone so that the *cannabis* can treat the area.

In another aspect, *cannabis* can be extracted and infused with oil and such infused *cannabis* can be used in one of: candy, baked good, popcorn, gummies, shampoo, conditioner, lotions, soaps, massage oils, lip balm, salad dressings, mayonnaise, margarine, sugar free food. The oil infused *cannabis* can also be used in one of: cosmetic good, medication, aerosol spray.

Advantages of the preferred embodiments may include one or more of the following. The process provides for efficient delivery of *cannabis* at a low cost. The resulting oil with *cannabis* is usable immediately and the effects are long lasting and near instant. The Oil is a healthy alternative to butter and all types of other oils, which allows vegans to enjoy *cannabis*. It can be eaten directly or put into many products. The *cannabis* can be delivered as a spray, dermal patch, slow release drug or as food such as hard candies, baked goods (brownies, cookies), popcorn, gummies, shampoo, conditioner, lotions, soaps, massage oils, lip balm, salad dressings, mayonnaise, and margarine. The oil can also be used for cosmetics and drugs.

BRIEF DESCRIPTION OF THE DRAWINGS

The invention will now be further and more particularly described, by way of example only, and with reference to the accompanying drawings in which.

DESCRIPTION

A delivery system is disclosed. The delivery system includes transdermal patches, aerosol sprays, or injectable needles/cannulas. The delivery system can handle water insoluble drugs like cannabinoids/cannabiol (CBD). Cannabinoids are a group of 21-carbon-containing terpenophenolic compounds produced uniquely by *Cannabis* species (e.g., *Cannabis sativa* L.), referred to as phytocannabinoids. Although delta-9-tetrahydrocannabinol (THC) is the primary psychoactive ingredient, other known compounds with biologic activity are cannabinol, cannabidiol (CBD), cannabichromene, cannabigerol, tetrahydrocannabivarin, and delta-8-THC. CBD, in particular, is thought to have significant analgesic and anti-inflammatory activity without the psychoactive effect (high) of delta-9-THC. Cannabinoids are effective in pain relief and curing certain types of cancer. Since cannabinoids are not easily water soluble there is a delayed in absorbance and the effect felt in patients for a slow release in the case of pain relief patches. The patches are compose of several thin layers assembled together and usually release one of several opioids through the skin for about 72 hours. In one embodiment, the injectable needles/cannulas are 3D printed hyaluronic acid structures that are hard structures prior to use and when in use, the hyaluronic acid expands upon contact with liquid and create a delivery pathway.

Figure 1:
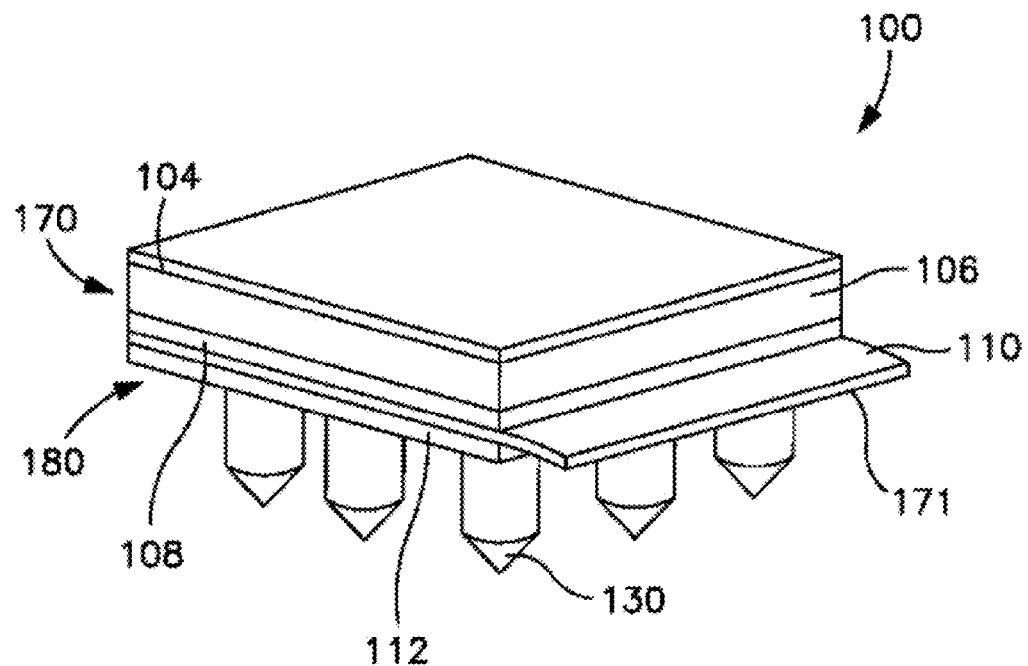
FIGS. 1-2 show an exemplary transdermal patch.
Figure 2:
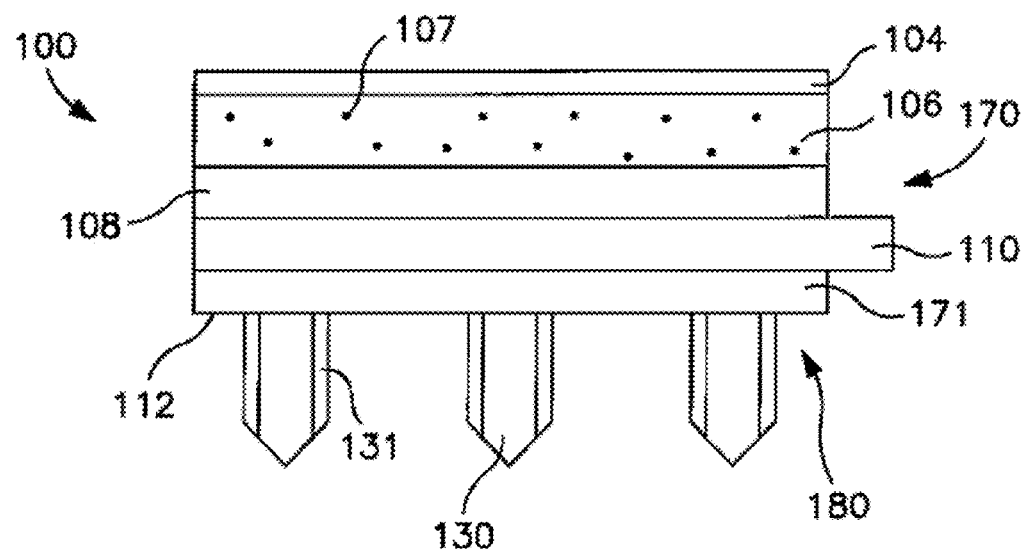

FIGS. 1-2 show an exemplary transdermal patch 100 that provides efficacy benefits and can maintain a steady level of medication for a number of days. One exemplary patch uses slow release medication embedded in hyaluronic acid (HA) with hydrophobic molecules that can permeate through the lipid pathway. The physiological factors that affect drug absorption include skin age, gender, ethnicity, the thickness of the stratum corneum (which varies between different anatomical sites), the degree of skin hydration, the presence of hair follicles, skin condition (e.g., disease compromises the natural barrier function of the skin), temperature, and metabolism. In terms of physicochemical factors, properties such as drug solubility, partition coefficient, molecular mass, and whether the drug is in an ionized or unionized form will influence transdermal absorption.

The transdermal patch 100 that contains a drug delivery assembly 170 and a microneedle assembly 180 containing a plurality of needles made from hyaluronic acid (HA). In a first state, the HA is a solid that can penetrate the skin. In a second state, with liquid, the HA becomes expanded to release drug/medication into the skin penetration to deliver drug or solution. The drug delivery assembly 170 includes a reservoir 106 positioned adjacent to a rate control membrane 108, such as described above. Although optional, the assembly 170 also contains an adhesive layer 104 that is positioned adjacent to the reservoir 106. The microneedle assembly 180 likewise includes a support 112 from which extends a plurality of microneedles 130 having channels 131, such as described above. The layers of the drug delivery assembly 170 and/or the microneedle assembly 180 may be attached together if desired using any known bonding technique, such as through adhesive bonding, thermal bonding, ultrasonic bonding, etc.

Regardless of the particular configuration employed, the patch 100 also contains a release member 110 that is positioned between the drug delivery assembly 170 and the microneedle assembly 180. While the release member 110 may optionally be bonded to the adjacent support 112 and/or rate control membrane 108, it is typically desired that it is only lightly bonded, if at all, so that the release member 110 can be easily withdrawn from the patch 100. If desired, the release member 110 may also contain a tab portion 171 that extends at least partly beyond the perimeter of the patch 100 to facilitate the ability of a user to grab onto the member and pull it in the desired direction. In its "inactive" configuration as shown in FIGS. 1-2, the drug delivery assembly 170 of the patch 100 securely retains a drug compound 107 so that it does not flow to any significant extent into the microneedles 130. As indicated above, the patch can be "activated" by simply applying a force to the release member so that it is detached from the patch. The detachment of the release member immediately initiates the flow of the drug compound to the microneedles because the drug delivery assembly is already disposed in fluid communication with the microneedle assembly. In certain embodiments, the microneedle assembly is not initially in fluid communication with the drug delivery assembly. When it is desired to use the patch, the user may physically manipulate the two separate assemblies into fluid communication. The release member may be separated either before or after such physical manipulation occurs. The hyaluronic acid microneedle structures that are hard structures prior to use and when in use, the hyaluronic acid expands upon contact with skin pores or body liquid and create a delivery pathway.

The patch is ideal for the management of perioperative pain and chronic pain in patients suffering from conditions like diabetes and cancer. Another application is during vaccination for babies. The patch can be applied on the baby's arm five minutes before the jab, for the painkiller to set in. In this way, vaccination can potentially be painless for babies. The patch can also deliver collagen for cosmetic and skincare purposes and for artificial skin replacement after a burn or accident, for example. The collagen can be encapsulated in the microneedles and delivered up to the dermis layer of the skin, while current skincare products can only deliver to the outermost layer of skin. The patch can also deliver botox through the large pores from the HA microneedles.

The number of microneedles shown in the figures is for illustrative purposes only. The actual number of microneedles used in the patch may, for example, range from about 500 to about 10,000, in some embodiments from about 2,000 to about 8,000, and in some embodiments, from about 4,000 to about 6,000. The size and shape of the microneedles may also vary as desired. For example, the microneedles have an overall conical shape. In alternative embodiments, however, the microneedles 318 may have an overall pyramidal shape or a cylindrical portion upon which is positioned a conical portion having a tip. The tip typically has a radius that is less than or equal to about 1 micrometer. The microneedles are typically of a length sufficient to penetrate the stratum corneum and pass into the epidermis, but not penetrate through the epidermis and into the dermis in applications where it is desirable to minimize pain. In certain embodiments, the microneedles have a length (from their tip to their base) of about 500 micrometers or less, in some embodiments from 1 to about 400 micrometers, and in some embodiments, from about 50 to about 350 micrometers.

The drug delivery assembly of the transdermal patch contains a reservoir that can initially retain a drug compound. The term "reservoir" generally refers to a designated area or chamber configured to retain a fluidic drug compound. The reservoir may be an open volume space, gel, solid structure, etc. Nevertheless, in most embodiments, the reservoir is a solid matrix through which the drug compound is capable of flowing. The selection of the desired materials for the matrix typically depends on the solubility and diffusivity of the target drug compound and the time during which release is sought. In one embodiment, for example, the solid matrix is generally impermeable to the compound, and the material used to form the matrix is selected so that the drug compound is able to diffuse therethrough. In other embodiments, however, the solid matrix may be permeable or semi-permeable to the drug compound so that it can simply flow through its pores. Examples of such solid matrices include porous fiber webs (e.g., woven or nonwoven), apertured films, foams, sponges, etc. Regardless of its particular form, polymeric materials are often used to form the solid matrix, such as silicones, acrylic resins, acetate copolymers (e.g., ethylene vinyl acetate), plasticized polyvinyl acetate/polyvinyl chloride resins, plasticized hydrolyzed polyvinyl alcohol, rubber-based adhesives (e.g., polyisobutylenes extended with a solvent such as mineral oil), plasticized polyvinyl chloride, polyethylene glycols and polypropylene glycols of varying molecular weights, cellulose esters, polyolefins; etc.

There is no particular limitation to the drug compounds that may be retained within the reservoir and employed in the patch of the present invention. Suitable compounds may include, for instance, proteinaceous compounds, such as insulin, immunoglobulins (e.g., IgG, IgM, IgA, IgE), TNF-α, antiviral medications, etc.; polynucleotide agents, such as plasmids, siRNA, RNAi, nucleoside anticancer drugs, vaccines, etc.; small molecule agents, such as alkaloids, glycosides, phenols, etc.; anti-infection agents, hormones, drugs regulating cardiac action or blood flow, pain control; and so forth. A non-limiting listing of agents includes anti-Angiogenesis agents, anti-depressants, antidiabetic agents, antihistamines, anti-inflammatory agents, butorphanol, calcitonin and analogs, COX-II inhibitors, dermatological agents, dopamine agonists and antagonists, enkephalins and other opioid peptides, epidermal growth factors, erythropoietin and analogs, follicle stimulating hormone, glucagon, growth hormone and analogs (including growth hormone releasing hormone), growth hormone antagonists, heparin, hirudin and hirudin analogs such as hirulog, IgE suppressors and other protein inhibitors, immunosuppressives, insulin, insulinotropin and analogs, interferons, interleukins, leutenizing hormone, leutenizing hormone releasing hormone and analogs, monoclonal or polyclonal antibodies, motion sickness preparations, muscle relaxants, narcotic analgesics, nicotine, non-steroid anti-inflammatory agents, oligosaccharides, parathyroid hormone and analogs, parathyroid hormone antagonists, prostaglandin antagonists, prostaglandins, scopolamine, sedatives, serotonin agonists and antagonists, sexual hypofunction, tissue plasminogen activators, tranquilizers, vaccines with or without carriers/adjuvants, vasodilators, major diagnostics such as tuberculin and other hypersensitivity agents. Vaccine formulations may include an antigen or antigenic composition capable of eliciting an immune response against a human pathogen or from other viral pathogens.

Due to its controlled capillary flow, the patch can deliver high molecular weight drug compounds such as botox. The term "high molecular weight" generally refers to compounds having a molecular weight of about 1 kiliDalton ("kDa") or more, in some embodiments about 10 kDa or more, in some embodiments about 20 kDa to about 250 kDa, and in some embodiments, from about greater than about 40 kDa to about 150 kDa. Examples of such high molecular weight compounds include protein therapeutics, which refers to any biologically active proteinaceous compound including, without limitation, natural, synthetic, and recombinant compounds, fusion proteins, chimeras, and so forth, as well as compounds including the 20 standard amino acids and/or synthetic amino acids. In one particular embodiment, the patch may be utilized in treatment of a chronic condition, such as rheumatoid arthritis ("RA"), to deliver a steady flow a drug to a subject in need thereof. RA drug compounds may include symptom suppression compounds, such as analgesics and anti-inflammatory drugs including both steroidal and non-steroidal anti-inflammatory drugs (NSAID), as well as disease-modifying antirheumatic drugs ("DMARD"). The patch can include and deliver symptom suppression compounds, such as analgesics and anti-inflammatory drugs, as well as DMARD compounds, including biological DMARDs. Through utilization of the transdermal patch of the present invention, RA drugs can be delivered at a steady concentration over a sustained period. The patch can prevent the initial burst of concentration common when utilizing previously known methods for delivery of RA drugs, including oral delivery and injection.

One embodiment uses microneedles between 20 um to 1000 um in length, capable of puncturing the outermost layer of the epidermis (stratum corneum) to create openings, or pores, relative to the size of the active pharmaceutical agent being administered, in this situation this being the *cannabis* agent, in which the ingredients can be delivered. This allows for the increase of permeability and decrease skin sensation when an agent is administered. However, there has been research on increased permeation of mostly water-soluble compounds through microneedle-treated aqueous pores, rather than an oil based agent such as cannabidiols.

An embodiment example shown here comprises a pharmaceutical composition comprising a cannaboid, or cannabinoid prodrug incorporated into a hydrogel which is used in conjunction with a microneedle array for the treatment of the targeted disease or condition that is responsive to a cannabiod. Another possible embodiment consists of a microneedle array in which the pharmaceutical composition consists of a cannabidiol prodrug that consists of a COX inhibitor and/or a penetration enhancer.

Used here, "cannabinoid" includes any compound that interacts with a cannabinoid receptor and various cannabinoid mimetics such as certain tetrahydropyran analogs. However, dues to its highly lipophilic nature, cannabidiol is poorly absorbed through membranes such as the skin of mammals, including humans. Because of this, successfully trandermally administering effective quantities of cannabidiol to a mammal needs a reasonable amount of time and certain amount of surface area.

In one embodiment, the composition to be put in the microneedle will comprise a cannaboid, such as cannabidiol or the cannabidiol prodrug, in a total amount weight of the composition of about 0.1% to about 95%. Microneedles can be solid or hollow and are made from many bio-compatible materials, including silicon, biodegradable polymers, and stainless steel. Solid microneedles can be used to create channels of pores in the skin, followed by an application of a transdermal patch to the skin surface. Alternatively, solid microneedles can be first coated with an active pharmaceutical agent and then inserted into the skin. Hollow microneedles can also be used to facilitate active permeation through the pore in the microneedle and into the skin. [0069] Many studies have shown that solid microneedles can increase skin permeability by up to four orders of magnitude of compounds ranging in size from small molecules to proteins to nanoparticles. This is good news because the size of the cannabidiols will be able to be used with the microneedle and be administered into the skin. The terminology "pharmaceutical composition" used here includes any ointment, cream, solution, suspension, lotion, paste, gel, hydrogel, spray, foam, solid or oil which may be created or forms and used to administer a cannabinoid or cannabinoid prodrug [0086]. One embodiment may contain a penetration enhancing agent or co-solvent for transdermal to topical delivery. A penetration enhancer is an excipient that aids in the diffusion of active component through the stratum corneum of the skin. Many penetration enhancers also function as co-solvents, which are thought to increase the solubility of the cannaboid in the composition and enhance drug delivery through the microneedle-created pores in the skin. Appropriate enhancers to be used should be; highly potent (with a specific mechanism of action), demonstrate a rapid onset upon administration, have a predictable duration of action, have only non-permanent or reversible effects on the skin, be chemically stable, (vi) have no or minimal pharmacological effects; (vii) be physically and chemically compatible with other compositions, (viii) be odorless; (ix) be colorless; (x) be hypoallergenic; (xi) be non-irritating; (xii) be non-phototoxic; (xii) be non-comedogenic; (xiv) have the solubility parameter approximating that of the skin (10.5 cal/cm3); (xv) be readily available; (xvi) be inexpensive; and (xvii) be able to be formulated in compositions for topical or transdermal delivert of an active pharmaceutical agent.

Other drugs can be in the patch. For example, RA drugs that may be incorporated in the patch can include, without limitation, one or more analgesics, anti-inflammatories, DMARDs, herbal-based drugs, and combinations thereof. Specific compounds can, of course, fall under one or more of the general categories described herein. For instance, many compounds function as both an analgesic and an anti-inflammatory; herbal-based drugs can likewise function as a DMARD as well as an anti-inflammatory. Moreover, multiple compounds that can fall under a single category can be incorporated in the patch. For instance, the patch can include multiple analgesics, such as acetaminophen with codeine, acetaminophen with hydrocodone (vicodin), and so forth. Examples of analgesics and/or NSAIDs include analgesics available over the counter (OTC) at relatively low dosages including acetamide (acetaminophen or paracetamol), acetylsalicylic acid (aspirin), ibuprofen, ketoprofen, naproxen and naproxen sodium, and so forth. Prescription analgesics and/or anti-inflammatories can include, without limitation, OTC analgesics at concentrations requiring a prescription, celecoxib, sulindac, oxaprozin, salsalate, piroxicam, indomethacin, etodolac, meloxicam, nabumetone, keteroloc and ketorolac tromethamine, tolmetin, diclofenac, diproqualone, and diflunisal. Narcotic analgesics can include codeine, hydrocodone, oxycodone, fentanyl, and propoxyphene.

DMARDs can encompass both small molecule drugs and biological agents. DMARDs may be chemically synthesized or may be produced through genetic engineering processes (e.g., recombinant techniques). Chemically synthesized DMARDs encompassed herein include, without limitation, azathioprine, cyclosporine (ciclosporin, cyclosporine A), D-penicillamine, gold salts (e.g., auranofin, Na-aurothio-malate (Myocrism), chloroquine, hydroxychloroquine, leflunomide, methotrexate, minocycline, sulphasalazine (sulfasalazine), and cyclophosphamide. Biological DMARDs include, without limitation, TNF-α blockers such as etanercept (Enbrel®), infliximab (Remicade®), adalimumab (Humira®), certolizamab pego (Cimzia®) and golumumab (Simponi™); IL-1 blockers such as anakinra (Kineret®); monoclonal antibodies against B cells including rituximab (Rituxan®); T cell costimulation blockers such as abatacept (Orencia®), and IL-6 blockers such as tocilizumab (RoActemra®, Actemra®); a calcineurin inhibitor such as tacrolimus (Prograf®). The patch may also incorporate multiple RA drugs. For instance, the patch can include a combination of DMARDs in addition to an analgesic and/or an anti-inflammatory drug. Common combinations of DMARDs include, for example, methotrexate in combination with hydroxychloroquine, methotrexate in combination with sulfasalazine, sulfasalazine in combination with hydroxychloroquine, and all three of these DMARDs together, i.e., hydroxychloroquine, methotrexate, and sulfasalazine.

If desired, the patch may employ a plurality of reservoirs for storing multiple materials for delivery. The reservoirs may be positioned adjacent to each other, either in a vertical or horizontal relationship. For instance, a first reservoir may contain a drug compound and a second reservoir may contain an excipient (e.g., delivery vehicle, such as alcohols, water, etc.; buffering agents; and so forth). In one particular embodiment, for example, the first reservoir may contain a lyophilized powder of the drug compound (e.g., RA drug) and the second reservoir may contain an aqueous solution for reconstituting the powder. Alternatively, multiple reservoirs may be employed that each contains a drug compound. Regardless, the different materials may be mixed prior to delivery.

The drug delivery assembly also contains a rate control membrane that is in fluid communication with the drug reservoir. The rate control membrane can help slow down the flow rate of the drug compound upon its release. Specifically, fluidic drug compounds passing from the drug reservoir to the microneedle assembly may experience a drop in pressure that results in a reduction in flow rate. If this difference is too great, some backpressure may be created that can impede the flow of the compound and potentially overcome the capillary pressure of the fluid through the microfluidic channels. Thus, the use of the rate control membrane can ameliorate this difference in pressure and allow the drug compound to be introduced into the microneedle at a more controlled flow rate. The particular materials, thickness, etc. of the rate control membrane can vary based on multiple factors, such as the viscosity of the drug compound, the desired delivery time, etc.

The rate-controlling membrane may be fabricated from permeable, semi-permeable or microporous materials that are known in the art to control the rate of drug compounds and having a permeability to the permeation enhancer lower than that of drug reservoir. For example, the material used to form the rate control membrane may have an average pore size of from about 50 nanometers to about 5 micrometers, in some embodiments from about 100 nanometers to about 2 micrometers, and in some embodiments, from about 300 nanometers to about 1 micrometer (e.g., about 600 nanometers). Suitable membrane materials include, for instance, fibrous webs (e.g., woven or nonwoven), apertured films, foams, sponges, etc., which are formed from polymers such as polyethylene, polypropylene, polyvinyl acetate, ethylene n-butyl acetate and ethylene vinyl acetate copolymers.

If desired, the drug delivery assembly may contain additional layers or materials that provide various benefits to the resulting transdermal patch. In one embodiment, for example, the assembly includes an adhesive layer that can help facilitate the attachment of the patch to a user's skin during use. Although not required, the adhesive layer is often disposed over the reservoir. The adhesive layer typically employs an adhesive coated onto a backing material. The backing may be made of a material that is substantially impermeable to the drug compound, such as polymers, metal foils, etc. Suitable polymers may include, for instance, polyethylene terephthalate, polyvinylchloride, polyethylene, polypropylene, polycarbonate, polyester, and so forth. The adhesive may be a pressure-sensitive adhesive as is known in the art. Suitable adhesives may include, for instance, solvent-based acrylic adhesives, solvent-based rubber adhesives, silicone adhesives, etc.

A large percentage of receptors to which CBD has affinity to are found in the skeletal sympathetic nerve terminals. CBD is non-psychoactive and therefore can be safely give without affects. It has shown to stimulate the coding through the mRNA expression of a particular enzyme that helps catalyzes lysine hydroxylation which results in collagen crosslinking in bones. This system is part of the autonomic nervous system which is largely responsible for the body's fight-or-flight response and maintain homeostasis (psychological balance).

When these receptors get activated by compounds like CBD it triggers and accelerates the natural healing process. As the aging process occurs, the body's ability to heal fractures slows down drastically. The hydroxylation of lysine does not occur as readily and affects the amount of crosslinking. In people over 65, fractures account for a third of that populations nonfatal injuries and two-thirds of non-fatal care cost. A simple fall can result in serious bone injury. The administration of natural extracted or synthetic CBD to older patients who have suffer from bone fractures can speed up the healing process and minimizing any immobility brought by the fracture. Injections or a patch containing CBD or a synthetic can be administrated at the site to ensure the maximum compound concentration can be reached. Since the natural deviated CBD is not readily soluble in water, a greater concentration may be needed to ensure that enough gets deliver to the sympathetic nerve endings.

A CBD patch can be produced in a variety of shapes, sizes and concentration to accommodate the span of the fracture area. Similar to pain relief patches, the product will be composed of different layer in which the active ingredient is infused into a membrane that will be in contact with the skin. The active ingredient (CBD or synthetic) will be slowly absorbed by the skin into the system and provide a steady release of compounds that ensure the activation of bone formation and prevent malformations, which can introduce more structural complications, during healing. The patch will have enough active ingredient for a few days (~3) and easily replaced with a new one. This is noninvasive method of treatment with low maintenance since it will have a water proof coating and flexible to accommodate the human structure. As well, the patch can be also infused with an opium for pain relief. This duel product in one can aid the heeling process while also offering some pain relief.

CBD cannot only heal bone fractures but also has the potential to increase the bone mineral density (decreases with age and in certain medical conditions). The bone mineral density is used as an indicator for osteoporosis and fracture risk which increases in age. Injections or oral capsules can be administered for those at risk for low bone mineral density to help stimulate bone formation and decrease the likelihood of a serious bone injury. In medical conditions like in Type 1 Diabetes Mellitus (T1DM), bone complications can arise and resulting in low bone mineral density. In particular, women on the onset of menopause (~40) has an increase difficulty in absorbing calcium for bone formation resulting in fragile bones.

As well, CBD can be used in toothpaste and help strength the root of teeth.

In another aspect, CBD can be delivered by mixing blended *cannabis* material with fat; identifying cancerous cells in a body; and contacting the fat *cannabis* into the body portion with cancerous cells.

In yet another aspect, a method for infusing *cannabis* with plant or vegetable oil, comprising mixing about 230 grams of *cannabis*, about ½ pound plant or vegetable oil, about 5-7 cups of water, sugar leaf and bud plant parts to form a mixture; boiling the mixture in a magnetic pot and decarboxylating the mixture to form a decarboxylated mixture; straining the decarboxylated mixture and after pressing the decarboxylated mixture dry to form a dry mixture, providing boiling water to the dry mixture to form an aqueous mixture in a second pot and boiling the aqueous mixture; cooling the aqueous mixture and removing a top oily layer floating to the top of the cooled aqueous mixture; placing the top oily layer in a cup; and placing the cup surrounded by a different oil and then boiling the cup in the different oil until water evaporates leaving oil infused *cannabis*.

In another aspect, a slow release system using HA and a drug is disclosed. The HA is cross-linked to provide predetermined dissolution to release the medication in different layers of HA for release over time.

In another aspect, CBD can be delivered by mixing blended *cannabis* material with hyaluronic acid (HA); cross-linking the HA to provide a slow release *cannabis*; identifying cancerous cells in a body; and contacting the HA infused with *cannabis* into the body portion with cancerous cells for time release.

In another aspect, oil infused *cannabis* can be used in one of: candy, baked good, popcorn, gummies, shampoo, conditioner, lotions, soaps, massage oils, lip balm, salad dressings, mayonnaise, margarine, sugar free food. The oil infused *cannabis* can also be used in one of: cosmetic good, medication, aerosol spray. Cannabinoids like cannabiol (CBD) provide two cannabinoid receptors, CB1 and CB2 that are activated by Δ-9-tetrahydrocannabinol (THC), which is the principal psychoactive compound found in *cannabis*. In addition, CBD has a low affinity to cannabinoid receptors and hence is non-psychoactive. CBD like other cannabinoids are soluble in non-polar organic solvents. Similarly, CBD can be infused into oil solvents like avocado oil. Due to the non-water solubility nature of cannabinoids, they do not interact very well with the aqueous environment of the blood stream and tissues. To address this issue, CDB is infused in hyaluronic acid (HA) and the result is placed inside the body or dermally on the skin. As CBD or THC is not hydrophilic, but HA is hydrophilic, HA can bind better to the organ or tissue and then the CDB or THC can interact with the aqueous environment in the blood stream and tissues. However, this approach should not be used to treat cancer as HA can encourage cancer growth.

The microneedle device fabrication processes avoid exposing a biopolymer and a set of biosubstances carried thereby to processing environments/equipment/conditions/energies, reactive species, and/or chemical substances/species associated with conventional micron scale manufacturing or fabrication processes which would present a significant likelihood or risk of adversely affecting biosubstance integrity or viability. Multiple embodiments in accordance with the present disclosure avoid exposing one or more biosubstances carried by a biopolymer to unnecessarily or undesirably high temperature(s) (e.g., at which significant protein denaturation is expected to occur), for instance, temperatures significantly exceeding room temperature, such as temperatures above approximately 40° C., temperatures above approximately 30° C., or temperatures above or significantly above room temperature such as a temperature beyond approximately 27° C.).

In some embodiments, a microneedle forming biopolymer can include both PEGDA and gelatin (e.g., which can form a biosubstance delivery matrix within the microneedles). A support member such as one of more of a glass, quartz, plastic, or other hard material that can be surface treated such that (a) a support member surface can firmly couple or chemically bond directly to a layer of microneedle forming biopolymer carried by the support member surface; and (b) microneedles that are fabricated by way of selectively or preferentially cross-linking portions of the microneedle forming biopolymer layer (such as HA layer) remain firmly coupled or chemically bonded to the support member itself. Hence, in such embodiments, microneedles are not bonded to a biocompatible polymer backing layer carried by a support member, but rather are bonded to one or more surface treated portions of the solid member itself. Consequently, microneedle fabrication occurs by way of selectively directing electromagnetic energy through the support member and into portions of the microneedle forming biopolymer layer carried thereby (e.g., by way of directing UV light (a) toward, to, and through a set of openings in a photomask disposed adjacent or upon the support member; (b) through portions of the support member corresponding to such openings; and (c) into corresponding portions of the microneedle forming biopolymer layer carried by and bonded to the support member). Other embodiments can include a backing structure having a surface that includes (a) a first surface area or region that includes a biocompatible polymer backing layer; and (b) a second surface area or region that excludes a biocompatible polymer backing layer. Microneedles can be bonded to and fabricated on each such surface area in a manner that is identical, substantially identical, or analogous to that described above.

Transdermal patches can include reservoir devices, matrix devices, multiple polymer devices, and multilayer matrix systems. The reservoir system is a diffusion-controlled system, which contains a drug reservoir with a rate-controlling polymer membrane. With this device, the membrane that lies between the drug reservoir and the skin controls the rate of release from the drug reservoir to the skin surface. For matrix patches, the active is mixed with or contained in a polymer, the drug is released at a rate governed by the components in the matrix. For a drug-in-adhesive matrix, the polymer (in which the drug is dispersed) is an adhesive. The adhesive serves two roles—it acts as the drug reservoir, and it holds the patch on the skin.

Preferably, chemical enhancers, iontophoresis, and non-cavitational ultrasound can be used to increase skin permeability. Other transdermal delivery systems can target the stratum corneum using microneedles, thermal ablation, microdermabrasion, electroporation, and cavitational ultrasound to enable more effective transdermal delivery, while still protecting the deeper tissues.

Other skin permeabilization techniques, including low-frequency sonophoresis and electroporation, have been studied further to refine their role in enhancing delivery through skin. Modulated delivery (i.e., controlled amount of dose) is possible using iontophoresis when an appropriate amount of current is applied over a stipulated time duration. Physical enhancement techniques have thus expanded the scope of transdermal delivery and have a promising future The micro-needles on the patch create micrometer-sized porous channels in the skin, thereby, enabling rapid drug delivery. Because the needle shafts are approximately 600 μm in length, they do not cause any perceptible pain. The reservoir system in the patch acts as channels for drugs to be encapsulated in the backing layers, circumventing the premature closure of miniaturized pores created by the microneedles and ensuring continued drug permeation.

One embodiment forms microneedles, which are less than 0.5 mm high or smaller, from a hydrogel of biocompatible polymers that can safely deliver constant doses of the drug. The microneedles are hard and sharp when dry, but rapidly hydrate when inserted into the skin. The swollen hydrogel projections create a continuous aqueous pathway between the external environment and dermal microcirculation enabling controlled delivery of the API. In other embodiments, the microneedle array consists of a sheet arrayed with 100-2000 μm projections made of polysaccharides. The drug is delivered into the body by simply attaching the sheet onto the skin. These projections dissolve in the skin within minutes as the drug is delivered.

In one embodiment, THC can be used to treat glioblastoma multiforme (GBM), a malignant primary brain tumor. In one embodiment, the THC administered composition is as follow: 96.5% THC, 1.5% of Δ8-THC, 0.5% butyl-THC, and propyl-THC. The patient first undergoes a surgical procedure to make a cavity in the brain, and then THC treatment is as follows:
1. A cavity and incision are made surgically near tumor tissue
2. A silastic infusion catheter is inserted inside cavity, portion of the catheter will be left accessible on the outside
3. Connected to catheter is a subclavicular reservoir
4. 100 mg (THC solution)/ethanol is dissolved in 30 mL physiological saline solution with 0.5% weight/volume human serum albumin
5. Syringe pump transfers 0.3 mL/min of the THC solution to the subcutaneous reservoir.

On the first day the dosage given is 20-40 μg, depending on side effects observed. The amount can be slowly increased to 80-180 μg per day for 2-5 days. THC solution is administered on an average of 15 days per patient.

Due to the chemical structure of cannabinoids, they do not easily interact with the hydrophilic nature of tissues and cell membranes. As a result they do not travel far in deep tissues if inject directly into the blood stream and therefore not a very effective method. A more viable option is applying directly to the needed area through the usage of a catheter or similar mechanism. This would allow a greater concentration to be absorbed by cells. This is easier when the target is are easily located and accessible. As well, some synthesized cannabinoid compounds such as cannabinoid quinones have proven to be more water soluble than their naturally occurring counterparts. As a result it will be more quickly absorbed by the tissues and needing less of the active ingredient. An ideal synthetic compound would have the therapeutic properties observed in studies, have no psychoactive affects (no affinity for CB1 receptor) and high human absorption.

Cannabinoids may cause antitumor effects by various mechanisms, including induction of cell death, inhibition of cell growth, and inhibition of tumor angiogenesis invasion and metastasis. Cannabinoids appear to kill tumor cells but do not affect their nontransformed counterparts and may even protect them from cell death. For example, these compounds have been shown to induce apoptosis in glioma cells in culture and induce regression of glioma tumors in mice and rats, while they protect normal glial cells of astroglial and oligodendroglial lineages from apoptosis mediated by the CB1 receptor. The effects of delta-9-THC and a synthetic agonist of the CB2 receptor were investigated in HCC. Cannabinoids were shown to trigger cell death through stimulation of an endoplasmic reticulum stress pathway that activates autophagy and promotes apoptosis. CBD induced programmed cell death, independent of the CB1, CB2, or vanilloid receptors. CBD inhibited the survival of both estrogen receptor-positive and estrogen receptor-negative breast cancer cell lines, inducing apoptosis in a concentration-dependent manner while having little effect on nontumorigenic mammary cells.

Similar administration can be given in breast cancer treatment. In vivo and vitro studies have demonstrated the effectiveness of CBD and synthetic compounds with affinity to CB2 receptors to shrink breast tumors, and obstruct growth and metastasis in mice models. These compounds have demonstrated a specificity to target cancer cells and cytotoxicity test have shown no damage or toxics in other organs in the body. CBD can be administered after lumpectomy (removal of breast cancer tissue) to target any remaining cancer tissue and prevent metastasis. Administration is:
1. General anesthetic is administered, incision is made in the breast near where tumor was located and cavity is prepared
2. Small balloon-catheter is used and the soft balloon portion is inserted into cavity, Tip of catheter tube is left outside near incision. Balloon is filled with saline solution and secured
3. Exposed catheter is connected to syringe pump and appropriate dosage of CBD or synthetic dissolved in physiological saline solution
4. Syringe pump delivers final solution at desired rate for the duration of treatment time One use for medicinal *cannabis* in cancer treatment is for pain management. A study compared the therapeutic usage and effects of smoked marijuana and orally administered THC (dronabinol). The sensitivity and tolerance to pain were measured by having the participants take the cold-pressor test after administration. It was concluded that both marijuana and dronabinol decreased pain sensitivity. In dronabinol, however the decreased pain sensitivity affects were felt at a later time. On the average, with smoked *cannabis* the pain reduction affects were felt 15 minutes whereas with dronabinol it took 180 minutes after administration. However, dronabinol affects lasted longer than smoked marijuana. The orally administered THC used size 00 opaque capsules with a dosage of either 10 mg or 20 mg. Lactose was used as the filler in the capsules. Orally taken dronabinol can be an effective method to deliver *cannabis* material without harmful side effects. Additionally, there are avocado oil supplements in capsule form available for people. The avocado infused *cannabis* could similarly be administered to people undergoing cancer treatments to treat their pain and other side effects. This option could make it easier for patients to intake *cannabis* compounds during treatment if they cannot tolerant other methods.

Cannabinoids may also be used in the treatment of glaucoma, which is damage in the optic nerves as a result of increased eye pressure (intraocular pressure). While marijuana decreases intraocular pressure in both healthy and sickly eyes, this decrease in pressure can result in lower blood delivery to the optic nerves cause damage. Oral capsules or eye drops are options for administration. In particular, eye droplets containing THC and other cannabinoids have been investigated and have the potential to decrease eye pressure. Due to the high hydrophobic nature of cannabinoids, it is not easily absorbed by the eye. This is compensated by adding HA into the eye droplets formation which offers:
- soluble in an aqueous environment (eye membrane and tissue) and therefore lower concentration of active ingredient is needed
- reduce optic nerve damage
- Longer lasting affects Administration of eye drop containing HA and cannabinoids is as fallow:
1. Ensure clean environment, tilt head and look upward with both eyes
2. Pull down lower eye lid slightly while holding tip of eye drop bottle near eye with the second hand
3. Applied enough pressure to bottle to administered one drop into the eye, blink and close eye for a few seconds
4. Repeats for second eye The resulting oil with *cannabis* is usable immediately and the effects are long lasting and near instant if used sublingually. The Oil is a healthy alternative to butter and all types of other oils, which allows vegans to enjoy food. It can be eaten directly or put into many products including hard candies, baked goods (brownies, cookies), popcorn, gummies, shampoo, conditioner, lotions, soaps, massage oils, lip balm, salad dressings, mayonnaise, and margarine. The oil can be used in sugar free line of products to make them friendly for diabetic patients.

Oil was originally, and still is, extracted for cosmetic use because of its very high skin penetration and rapid absorption. After extraction, the oil with added *cannabis* for application in skin care products is refined, bleached, and deodorized, resulting in an odorless yellow oil. Like extra virgin olive oil, cold-pressed oil is unrefined and so retains the flavor and color characteristics of the fruit flesh.

The solution can be used on skin. Topically the *cannabis* infused oil is rubbed onto an affected area and because this contains no alcohol it is possible to put it on slightly open cuts without burning or irritation. Oil acts as a natural anti-inflammatory and contains multiple vitamins, minerals, antioxidants and when used in combination with *cannabis* has shown great success in the rate of healing. This is a holistic alternative to the multitude of harmful by-products found in many other items currently used by consumers.

The CBD can be used as a pharmaceutical formulation that are packaged for delivery in the form of a gel, a tablet, a liquid, a capsule or for vaporization. More preferably the combination of cannabinoids to be used as a pharmaceutical formulation are packaged for delivery sublingually or buccally, preferably as a sublingual or buccal spray. Advantageously the pharmaceutical formulation further comprises one or more carrier solvent/s. Preferably the carrier solvents are ethanol and/or propylene glycol. More preferably the ratio of ethanol to propylene glycol is between 4:1 and 1:4. More preferably still the ratio is 1:1.

The administration of a combination of cannabinoids such as THC and CBD could be administered to a patient either at the same time, wherein the cannabinoids would be contained in the same formulation. The cannabinoids could also be administered at separate times for example; a formulation containing CBD could be administered to a patient at a fixed time prior to a formulation containing THC in order to ameliorate some of the side effects of THC, which CBD is known to improve or vice versa. The two cannabinoids could also be administered consecutively to a patient if required.

Preferably the invention provides a combination of cannabinoids, which are present as one or more *cannabis* based medicine extract/s (CBME/s). In one embodiment the CBME/s are produced by extraction with supercritical or subcritical CO2. In an additional embodiment the CBME/s are produced by extraction from plant material by volatilization with a heated gas. Preferably the CBME/s contain all of the naturally occurring cannabinoids in the plant material. Alternatively synthetic or highly purified isolates of the cannabinoids can be used.

The arthritis treatment can include administering a combination of cannabinoids x and y, where x is selected from the group consisting of cannabidiol (CBD) and cannabidivarin (CBDV) and where y is selected from the group consisting of delta-9-tetrahydrocannabinol (THC) and tetrahydrocannabinovarin (THCV), wherein the ratio of x:y by weight is less than or equal to 19:1.

THC and CBD compounds are activated in order to have an affinity to receptors like CB1 and CB2 and an effect in people. In their natural form in raw *cannabis*, they are found as cannabinolic acids, THCA and CBDA. Both have an attached carboxylic acid on one of the fused rings. To activate, the compounds undergo decarboxylation to remove the carboxyl group, which can be done by applying high amounts of heat. This results in the final THC and CBD products and the release of one CO2 molecule. When *cannabis* material is smoked, the compounds undergo this carboxyl group loss as it is being consumed by the flame. For non-smoking application such as oral or injectable administration, this needs to be part of the processing and preparation of the product. In the case of *cannabis* infused fruit oil, the mixing of the two materials is carried at high temperatures, 100° C., which serves as a way for the cannabinoid to lose the carboxylic acid and to suspended the compounds in the solvent.

Figure 3:
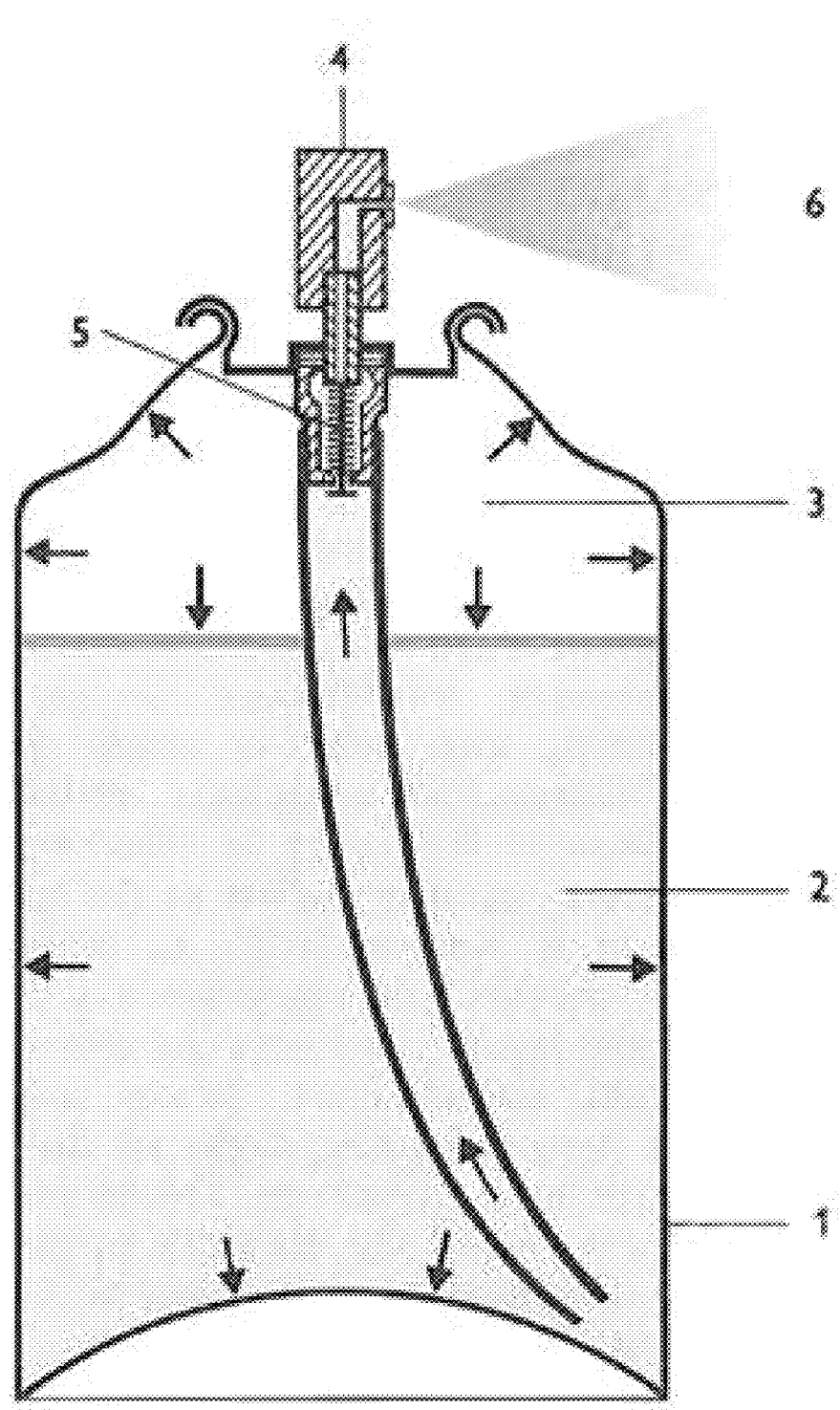
FIG. 3 shows a diagrammatic view of an apparatus for spraying a *cannabis* aerosol.

The *cannabis* infused oil can be used in an aerosol spray. FIG. 3 shows dispensing device for use with a pressurized aerosol-dispensing container 1. A can 1 contains the *cannabis* infused oil as the product 2, and compressed gas propellant 3 to propel the oil 2 through a tube. When the user presses on the dispensing head, compressed gas drives the oil through the tube where the oil exits at a nozzle of a spray head 4 as a mist of *cannabis* infused oil spray 6. Super saturation can be applied as transdermal spray, where supersaturated states are generated because volatile components (e.g., ethanol or isopropanol) evaporate after the spray is applied to skin, with consequent enhancement in skin flux.

In another embodiment, *cannabis* can be used in an electronic cigarette. An electronic cigarette battery with threading (such as the eGo-Twist or Vision Spinner) and a dry herb cartridge can be heated using a variable voltage battery so that the smoker can fine-tune the temperature to his/her liking. The vape pen herb cartridges will combust the herb, not vaporize it. A dry herb cartridge attachment will turn your e-cigarette into an electric pipe (or e-blunt). For vaporization, a laser with suitable power supply is used.

For inhalation, the formulations of the present invention may be delivered via any inhalation methods known to those skilled in the art. Such inhalation methods and devices include, but are not limited to, metered dose inhalers with propellants such as CFC or HFA or propellants that are physiologically and environmentally acceptable. Other included devices are breath-operated inhalers, multidose dry powder inhalers and aerosol nebulizers. One preferred way of administering the formulations of the invention is by using conventional actuators. The term "actuator" as used in the present invention includes all types of actuators presently available including but not limited to standard metered dose inhalers or breath operated inhalers. In another embodiment of the invention, administration is effected by a means of a pump or squeeze-actuated nebulizer. In more preferred embodiments of the invention administration is effected by means of a metered dose inhaler or an aerosol dispenser.

Formulations of the present invention may conveniently be present in unit dosage form and may be prepared by conventional pharmaceutical techniques as discussed above. Such techniques include the step of bringing into association the THC moiety and the pharmaceutical carrier(s) or excipient(s) In general the formulations are prepared by uniformly and intimately bringing into association the active ingredient with liquid carriers or finely divided solid carriers or both, and then, if necessary, shaping the product. While magnetic cook plate has been mentioned, a crockpot or a gas stove can be used. Depictions of various exemplary *cannabis* cookware and accessories as may be used with exemplary embodiments of the claimed invention are included in FIG. 3.

Avocados are one of the great cancer fighting foods, rich in a multiplicity of nutrients, including many potent antioxidants and phytochemicals as well as vitamins, minerals, fiber and monounsaturated healthy fats. Phytochemicals (plant chemicals) are defined as bioactive non-nutrient plant compounds in fruits, vegetables, grains, and other plant foods that have been linked to reducing the risk of major chronic diseases including cancer. Antioxidants and Phytochemicals found in avocados include:

Carotenoids: beta carotene, alpha carotene, zeaxanthin shown to inhibit the growth of prostate, breast and head and neck (oral) cancers.

Vitamin E is an antioxidant. Its role in cancer prevention is ambiguous due to several conflicting studies. Research suggests that the Vitamin E found in its natural form in foods such as avocados is indeed protective, while synthetic Vitamin E (alpha tocopherol acetate) supplements do not show this protective effect. The Nurses Health Study studied 83,234 women at baseline and sought to assess the incidence of breast cancer during a 14-year follow-up. The study showed that pre-menopausal women with a family history of breast cancer who consumed the highest quantity of vitamin E enjoyed a 43 percent reduction in breast cancer incidence compared to only a 16 percent risk reduction for women without a family history of breast cancer. The data indicates that some of the vitamin E compounds in food may account for the dramatic reductions in breast cancer incidence when dietary intake levels of vitamin E are measured.

Lutein: women with increased intake of lutein in their diets have been shown to have lower rates of breast cancer (Freudenheim J L, Marshall J R, Vena J E et al: Premenopausal breast cancer risk and intake of vegetables, fruits, and related nutrients. J Natl Cancer Inst 1996; 88(6):340-348.) Lutein is also found in high quantities in kale, broccoli and spinach.

Glutathione Glutathione is the body's master antioxidant. When liver glutathione levels rise, the liver is able to more effectively detoxify the body and protect the cells from oxidative stress. Whey protein also increases the glutathione levels of healthy cells while decreasing the glutathione levels of cancer cells.

Oleic Acid Avocados are also a source of fiber and oleic acid, a healthy monounsaturated fat. Oleic acid helps to lower unhealthy LDL plaque forming cholesterol. Increasing healthy dietary fats. Lowering cholesterol and body fat not only lead to reduced risk of cardiovascular disease but also lead to reduced inflammation and reduced cancer risk.

Oleic acid, the primary fat in avocados has been shown to offer significant protection against breast cancer. Women eating a diet rich in oleic acid have shown decreased rates of breast cancer. Oleic acid is also found in olives, olive oil, walnuts, almonds and pine nuts.

The phytochemicals listed above are all better absorbed in the presence of healthy fats and oils. Therefore the oleic acid in avocados not only helps the body to absorb and utilize the antioxidants also found within the avocado itself but contributes to the absorption of phytochemicals contained in other fruits and vegetables eaten at the same meal. Nature's design provides for optimum utilization of nutrients. One cup of Avocados also contains as much as 30 percent of your daily fiber intake as well as significant amounts of Vitamin K, Potassium, Folate, and Vitamin B6 all important to normal healthy cell function and cancer prevention.

The cannabinoids in marijuana slow cancer growth, inhibit formation of new blood cells that feed a tumor, and help manage pain, fatigue, nausea, and other side effects when cancer cells are exposed to tetrahydrocannabinol (THC), the principal psychoactive ingredient of marijuana. THC and other marijuana-derived compounds, known as "cannabinoids," are effective not only for cancer-symptom management (nausea, pain, loss of appetite, fatigue), they also confer a direct antitumoral effect.

In one treatment scenario, THC in oil slows tumor growth in common lung cancer and significantly reduces the ability of the cancer to spread. THC selectively targets and destroys tumor cells while leaving healthy cells unscathed. Conventional chemotherapy drugs, by contrast, are highly toxic; they indiscriminately damage the brain and body. The avocado based cannabinoids represent a class of anticancer drugs that retard cancer growth, inhibit angiogenesis [the formation of new blood cells that feed a tumor] and the metastatic spreading of cancer cells.

In another scenario, CBD is used as an inhibitor of breast cancer cell proliferation, metastasis, and tumor growth. The CBD kills breast cancer cells and destroys malignant tumors by switching off expression of the ID-1 gene, a protein that appears to play a major role as a cancer cell conductor. The ID-1 gene is active during human embryonic development, after which it turns off and stays off. But in breast cancer and several other types of metastatic cancer, the ID-1 gene becomes active again, causing malignant cells to invade and metastasize. The oil with cannabidiol, a potent antitumoral compound in its own right, acts synergistically with various anti-cancer pharmaceuticals, enhancing their impact while cutting the toxic dosage necessary for maximum effect.

*Cannabis* contains over 400 cannabinoid compounds and produces a wide spectrum of central and peripheral effects including alterations in cognition and memory, analgesic, anticonvulsive, and anti-inflammatory activities, and alleviation of intraocular pressure, nausea, and pain. It has also been demonstrated that cannabinoids have direct antitumor activity as well as immune response-associated antitumor activity. The antitumor activities involve different physiological pathways. For example, cannabinoids signal apoptosis by a pathway involving cannabinoid receptors, sustained ceramide accumulation, and Raf1/extracellular signal-regulated kinase activation.

The psychotropic principle of *cannabis* is delta-9-tetrahydrocannabinol (delta-9-THC), however, numerous medicinal properties of *cannabis* are thought to be associated with the acid metabolites of delta-9-THC, which show little or no psychoactivity. The physiological effects of the cannabinoids have been attributed to both receptor-mediated and non-receptor-mediated activities. Two types of cannabinoid receptors, CB1 and CB2, have been cloned in humans. The central cannabinoid receptor, CB1, is predominantly located in the central nervous system, although CB1 has also been detected in the gastrointestinal tract and other peripheral tissues. The CB2 receptor is predominantly found in the immune system. These receptors are members of the G-protein-coupled receptor superfamily (Pertwee, R. G., Pharmacol. Ther., 74(2): 129-180, 1997). CB1 and CB2 receptors have been demonstrated in prostate tissue. Recently, Ruiz-Llorente et al. (The Prostate, 54:95-102, 2003) have provided evidence that the CB1 receptor is functionally active in the human prostate gland.

The delta-9-THC inhibits specific binding of dihydroxytestosterone to the androgen receptor in the prostate gland, potentially regulating the serum levels of many sex hormones, thereby having an indirect antitumorigenic effect. Melck et al. (Endocrinology, 141:118-126, 2000) have shown that endocannabinoids, i.e. naturally occurring cannabinoids, inhibit prolactin-induced proliferation in the prostate cell line, DU-145, by inhibiting expression of prolactin receptors via a CB1-dependent mechanism. Ruiz et al. (FEBS Letters, 458:400-404, 1999) have shown that delta-9-THC causes apoptosis in the prostate cell line, PC-3. The apoptotic effect was similar to that apoptotic effect typically associated with ceramide accumulation. Ceramide has been implicated as an important second messenger regulating cell death. In prostate cells, ceramide has been shown to mediate apoptosis.

The analgesic and anti-inflammatory properties of delta-9-THC may be due to its acid metabolites (Burstein, S. H., Pharmacol. Ther., 82(1):87-96, 1999). Acid metabolites may result in an inhibition of eicosanoid synthesis; eicosanoids are mediators of inflammation. It has been postulated that the analgesic and anti-inflammatory properties are due to cannabinoid acids impacting on the arachidonic acid cascade by either causing an accumulation of free arachidonic acid or by inhibiting the synthesis of COX-2. COX-2 products are associated with inflammation. As a potential analgesic and anti-inflammatory therapeutic, it is of interest that chronic users of *cannabis* who are exposed to high blood levels of the delta-9-THC metabolite, delta-8-THC-11-oic acid, appear to be free from non-steroidal anti-inflammatory drug-type toxicity. This may be due in part to a selective inhibition of COX-2.

The prior art indicates that pharmaceuticals, phytochemicals, and nutraceuticals are available for treating disorders of the prostate by providing antioxidant activity, anti-inflammatory activity, and/or antitumorigenic activity. However, it is a concern that pharmaceuticals are expensive, have undesirable side effects, and generally require systemic application. It is a further concern that phytochemicals or extracts obtained from various plant sources can potentially contain toxins, may not be standardized, or may interact with other medications. Therefore, it would be advantageous to provide natural compositions for treatment of prostate disorders that lack toxic properties and that contain desirable therapeutically effective activities such as anti-inflammatory, antioxidant, as well as antitumorigenic activities. In this regard, extracts of *cannabis* plant material have been established to be non-toxic, and to have anti-inflammatory, antioxidant, and antitumorigenic properties in prostate tissue. Given the lack of toxicity of cannabinoids and the ability of the cannabinoids to protect prostate health by a myriad of distinct receptor-mediated and receptor-independent pathways by providing antioxidant protection, altering the conversion of testosterone to dihydroxytestosterone, inhibiting the binding of dihydroxytestosterone to androgen receptors, inducing apoptosis, and decreasing cellular proliferation, compositions containing *cannabis* extracts provide a therapeutically effective means of treating prostate disorders in patients in need thereof.

The phytocannabinoids described in the present application are listed below along with their standard abbreviations.

CBC Cannabichromene
CBCV Cannabichromenic acid
CBD Cannabidiol
CBDA Cannabidiolic acid
CBDV Cannabidivarin
CBG Cannabigerol
CBGV Cannabigerol propyl variant
CBL Cannabicyclol
CBN Cannabinol
CBNV Cannabinol propyl variant
CBO Cannabitriol
THC Tetrahydrocannabinol
THCA Tetrahydrocannabinolic acid
THCV Tetrahydrocannabivarin
THCVA Tetrahydrocannabivarinic acid The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids.

"Phytocannabinoids" are cannabinoids that originate from nature and can be found in the *cannabis* plant. The phytocannabinoids can be isolated cannabinoids or present as a botanical drug substance.

An "isolated cannabinoid" is defined as a phytocannabinoid that has been extracted from the *cannabis* plant and purified to such an extent that all the additional components such as secondary and minor cannabinoids and the non-cannabinoid fraction have been removed.

A "botanical drug substance" or "BDS" is defined in the Guidance for Industry Botanical Drug Products Draft Guidance, August 2000, US Department of Health and Human Services, Food and Drug Administration Centre for Drug Evaluation and Research as: "A drug derived from one or more plants, algae, or microscopic fungi. It is prepared from botanical raw materials by one or more of the following processes: pulverization, decoction, expression, aqueous extraction, ethanolic extraction or other similar processes." A botanical drug substance does not include a highly purified or chemically modified substance derived from natural sources. Thus, in the case of *cannabis*, BDS derived from *cannabis* plants do not include highly purified Pharmacopoeial grade cannabinoids.

"Endocannabinoids" are the cannabinoids that are produced endogenously by human or animal bodies. Up or down regulation of the endocannabinoid system may be useful in the treatment of some diseases or conditions.

"Synthetic cannabinoids" are compounds that have a cannabinoid-like structure yet are manufactured using chemical means. Depending on the method of manufacture the synthetic cannabinoid may comprise a racemic mixture of cannabinoids, in contrast to an isolated cannabinoid which will be a single enantiomer.

Phytocannabinoids can be found as either the neutral (decarboxylated form) or the carboxylic acid form depending on the method used to extract the cannabinoids. For example it is known that heating the carboxylic acid form will cause most of the carboxylic acid form to decarboxylate into the neutral form.

Phytocannabinoids can also occur as either the pentyl (5 carbon atoms) or propyl (3 carbon atoms) variant. Initially it was thought that the propyl and pentyl variants would have similar properties, however recent research has found that this may not be true. For example the phytocannabinoid THC is known to be a CB1 receptor agonist whereas the propyl variant THCV has been discovered to be a CB1 receptor antagonist meaning that it has almost opposite effects.

In the present invention a BDS is considered to have two components: the phytocannabinoid-containing component and the non-phytocannabinoid containing component. Preferably the phytocannabinoid-containing component is the larger component comprising greater than 50% (w/w) of the total BDS and the non-phytocannabinoid containing component is the smaller component comprising less than 50% (w/w) of the total BDS.

The amount of phytocannabinoid-containing component in the BDS may be greater than 55%, through 60%, 65%, 70%, 75%, 80% to 85% or more of the total extract. The actual amount is likely to depend on the starting material used and the method of extraction used.

The "principle phytocannabinoid" in a BDS is the phytocannabinoid that is present in an amount that is higher than that of the other phytocannabinoids. Preferably the principle phytocannabinoid is present in an amount greater than 40% (w/w) of the total extract. More preferably the principle phytocannabinoid is present in an amount greater than 50% (w/w) of the total extract. More preferably still the principle phytocannabinoid is present in an amount greater than 60% (w/w) of the total extract.

The amount of the principle phytocannabinoid in the BDS is preferably greater than 75% of the phytocannabinoid-containing fraction, more preferably still greater than 85% of the phytocannabinoid-containing fraction, and more preferably still greater than 95% of the phytocannabinoid-containing fraction.

In some cases, such as where the principle cannabinoid is either CBDV or THCVA the amount of the principle phytocannabinoid in the BDS is lower. Here the amount of phytocannabinoid is preferably greater than 55% of the phytocannabinoid-containing fraction.

The "secondary phytocannabinoid/s" in a BDS is the phytocannabinoid/s that is/are present in significant proportions. Preferably the secondary phytocannabinoid is present in an amount greater than 5% (w/w) of the total extract, more preferably greater than 10% (w/w) of the total extract, more preferably still greater than 15% (w/w) of the total extract. Some BDS's will have two or more secondary phytocannabinoids that are present in significant amounts. However not all BDS's will have a secondary phytocannabinoid. For example CBG BDS does not have a secondary phytocannabinoid in its extract.

The "minor phytocannabinoid/s" in a BDS can be described as the remainder of all the phytocannabinoid components once the principle and secondary phytocannabinoids are accounted for. Preferably the minor phytocannabinoids are present in total in an amount of less than 10% (w/w) of the total extract, more preferably still less than 5% (w/w) of the total extract, and most preferably the minor phytocannabinoid is present in an amount less than 2% (w/w) of the total extract.

Typically the non-phytocannabinoid containing component of the BDS comprises terpenes, sterols, triglycerides, alkanes, squalenes, tocopherols and carotenoids.

These compounds may play an important role in the pharmacology of the BDS either alone or in combination with the phytocannabinoid.

The "terpene fraction" may be of significance and can be broken down by the type of terpene: monoterpene or sesquiterpene. These terpene components can be further defined in a similar manner to the cannabinoids.

The amount of non-phytocannabinoid containing component in the BDS may be less than 45%, through 40%, 35%, 30, 25%, 20% to 15% or less of the total extract. The actual amount is likely to depend on the starting material used and the method of extraction used.

The "principle monoterpene/s" in a BDS is the monoterpene that is present in an amount that is higher than that of the other monoterpenes. Preferably the principle monoterpene/s is present in an amount greater than 20% (w/w) of the total terpene content. More preferably the principle monoterpene is present in an amount greater than 30% (w/w) of the total terpene content, more preferably still greater than 40% (w/w) of the total terpene content, and more preferably still greater than 50% (w/w) of the total terpene content. The principle monoterpene is preferably a myrcene or pinene. In some cases there may be two principle monoterpenes. Where this is the case the principle monoterpenes are preferably a pinene and/or a myrcene.

The "principle sesquiterpene" in a BDS is the sesquiterpene that is present in an amount that is higher than all the other terpenes. Preferably the principle sesquiterpene is present in an amount greater than 20% (w/w) of the total terpene content, more preferably still t greater than 30% (w/w) of the total terpene content. The principle sesquiterpene is preferably a caryophyllene and/or a humulene.

The sesquiterpene components may have a "secondary sesquiterpene". The secondary monoterpene is preferably a pinene, which is preferably present at an amount greater than 5% (w/w) of the total terpene content, more preferably the secondary terpene is present at an amount greater than 10% (w/w) of the total terpene content.

The secondary sesquiterpene is preferably a humulene which is preferably present at an amount greater than 5% (w/w) of the total terpene content, more preferably the secondary terpene is present at an amount greater than 10% (w/w) of the total terpene content.

Alternatively botanical extracts may be prepared by introducing isolated phytocannabinoids into a non-cannabinoid plant fraction as can be obtained from a zero cannabinoid plant or a CBG-free BDS.

In one implementation, a *cannabis* plant extract comprising a phytocannabinoid containing component and a non-phytocannabinoid containing component, is infused or mixed in oil for use in medicine, wherein the phytocannabinoid containing component comprises at least 50% (w/w) of the *cannabis* plant extract and the non-phytocannabinoid containing component comprises a monoterpene fraction and a sesquiterpene fraction, in which a principle monoterpene sub-fraction is selected from myrcenes or pinenes and a principle sesquiterpene sub-fraction is selected from caryophyllenes or humulenes.

In one implementation, a *cannabis* plant extract comprising a phytocannabinoid containing component and a non-phytocannabinoid containing component, is infused or mixed in oil for use in medicine, wherein the phytocannabinoid containing component comprises at least 50% (w/w) of the *cannabis* plant extract and the non-phytocannabinoid containing component comprises a monoterpene fraction and a sesquiterpene fraction, in which a principle monoterpene sub-fraction is selected from myrcenes or pinenes and a principle sesquiterpene sub-fraction is selected from caryophyllenes or humulenes.

Such *cannabis* infused oil can be used for treating a patient by administering a therapeutically effective amount of a *cannabis* plant extract comprising a phytocannabinoid containing component and a non-phytocannabinoid containing component, wherein the phytocannabinoid containing component comprises at least 50% (w/w) of the *cannabis* plant extract and the non-phytocannabinoid containing component comprises a monoterpene fraction and a sesquiterpene fraction, in which a principle monoterpene sub-fraction is selected from myrcenes or pinenes and a principle sesquiterpene sub-fraction is selected from caryophyllenes or humulenes to the patient.

Preferably principle monoterpene sub-fraction comprises myrcenes and the secondary monoterpene sub-fraction comprises pinenes. In another embodiment the principle monoterpene sub-fraction are both myrcenes and pinenes.

Preferably the principle sesquiterpene sub-fraction comprises caryophyllenes and secondary sesquiterpene sub-fraction comprises humulenes.

Preferably the principle phytocannabinoid is selected from the group consisting of: THCV, CBDV, CBGV, THCVA, THCA, CBDA, CBG, THC, CBD and CBC.

Preferably the non-phytocannabinoid containing component further comprises one or more compounds from the group consisting of: diterpenes; triterpenes; sterols; triglycerides; alkanes; squalenes; tocopherols; and carotenoids.

In one embodiment the *cannabis* plant extract comprises the principle phytocannabinoid CBG and the phytocannabinoid containing component comprises 61-75% (w/w) of the *cannabis* plant extract. Preferably the extract further comprises greater than 88% (w/w) CBG of the total phytocannabinoid fraction.

In a further embodiment the *cannabis* plant extract comprises the principle phytocannabinoid THC and the phytocannabinoid containing component comprises 77-94% (w/w) of the *cannabis* plant extract. Preferably the extract further comprises 78-95% (w/w) THC of the total phytocannabinoid fraction.

In a further embodiment the *cannabis* plant extract comprises the principle phytocannabinoid CBD and the phytocannabinoid containing component comprises 76-96% (w/w) of the *cannabis* plant extract. Preferably the extract further comprises 72-88% (w/w) CBD of the total phytocannabinoid fraction.

In a further embodiment the *cannabis* plant extract comprises the principle phytocannabinoid CBC and the phytocannabinoid containing component comprises 49-60% (w/w) of the *cannabis* plant extract. Preferably the extract further comprises 71-87% (w/w) CBC of the total phytocannabinoid fraction. More preferably the extract further comprises the secondary phytocannabinoids CBD and CBL. More preferably still the CBD comprises 6.5-8% (w/w) of the total phytocannabinoid fraction and the CBL comprises 5.8-7.1 (w/w) of the total phytocannabinoid fraction.

In a further embodiment the *cannabis* plant extract comprises the principle phytocannabinoid THCV and the phytocannabinoid containing component comprises 74-90% (w/w) of the *cannabis* plant extract. Preferably the extract further comprises 71-87% (w/w) THCV of the total phytocannabinoid fraction. More preferably the extract further comprises the secondary phytocannabinoid THC. More preferably still the THC comprises 14.8-18% (w/w) of the total phytocannabinoid fraction.

In a further embodiment the *cannabis* plant extract comprises the principle phytocannabinoid CBDV and the phytocannabinoid containing component comprises 64-78% (w/w) of the *cannabis* plant extract. Preferably the extract further comprises 52-64% (w/w) CBDV of the total phytocannabinoid fraction. More preferably the extract further comprises the secondary phytocannabinoids CBD and CBCV. More preferably still the CBD comprises 22.4-27.4% (w/w) of the total phytocannabinoid fraction and the CBCV comprises 5.5-6.7 (w/w) of the total phytocannabinoid fraction.

In a further embodiment the *cannabis* plant extract comprises the principle phytocannabinoid CBGV and the phytocannabinoid containing component comprises 54-66% (w/w) of the *cannabis* plant extract. Preferably the extract further comprises 68-84% (w/w) CBGV of the total phytocannabinoid fraction. More preferably the extract further comprises the secondary phytocannabinoid CBG. More preferably still the CBG comprises 19-23% (w/w) of the total phytocannabinoid fraction.

In a further embodiment the *cannabis* plant extract comprises the principle phytocannabinoid THCA and the phytocannabinoid containing component comprises 54-66% (w/w) of the *cannabis* plant extract. Preferably the extract further comprises 71-86% (w/w) THCA of the total phytocannabinoid fraction. More preferably the extract further comprises the secondary phytocannabinoid THC. More preferably still the THC comprises 13.4-16.4% (w/w) of the total phytocannabinoid fraction.

In a further embodiment the *cannabis* plant extract comprises the principle phytocannabinoid CBDA and the phytocannabinoid containing component comprises 71-86% (w/w) of the *cannabis* plant extract. Preferably the extract further comprises 78-86% (w/w) CBDA of the total phytocannabinoid fraction. More preferably the extract further comprises the secondary phytocannabinoid CBD. More preferably still the CBD comprises 6.1-7.5% (w/w) of the total phytocannabinoid fraction.

In a further embodiment the *cannabis* plant extract comprises the principle phytocannabinoid THCVA and the phytocannabinoid containing component comprises 62-75% (w/w) of the *cannabis* plant extract. Preferably the extract further comprises 53-65% (w/w) THCVA of the total phytocannabinoid fraction. More preferably the extract further comprises the secondary phytocannabinoid THCV. More preferably still the THCV comprises 17.3-21.2% (w/w) of the total phytocannabinoid fraction.

In a fourth aspect of the present invention there is provided one or more phytocannabinoids, either in an isolated form or in the form of a botanical drug substance (BDS), as a prophylactic or in the treatment of cancer In a fifth aspect of the present invention there is provided one or more phytocannabinoids taken from the group selected from: THCV, CBDV, THCVA, THCA, CBDA, CBD, CBG, and CBC, for use in the treatment of prostate cancer, wherein the THCVA is present as an isolated phytocannabinoid, the THCA, CBDA CBD, CBG or CBC are present in the form of a BDS, and the THCV or CBDV are present in either an isolated form or in the form of a BDS.

In accordance with a sixth aspect of the present invention there is provided the use of one or more phytocannabinoids taken from the group selected from: THCV, CBDV, THCVA, THCA, CBDA, CBD, CBG, and CBC, for use in the manufacture of a medicament to treat prostate cancer, wherein the THCVA is present as an isolated phytocannabinoid, the THCA, CBDA CBD, CBG or CBC are present in the form of a BDS, and the THCV or CBDV are present in either an isolated form or in the form of a BDS.

In accordance with a seventh aspect of the present invention there is provided a method of treating a patient with prostate cancer comprising administering an effective amount of one or more phytocannabinoids, selected from the group consisting of: THCV, CBDV, THCVA, THCA, CBDA, CBD, CBG, and CBC, wherein, where present, the THCVA is present as an isolated phytocannabinoid, the THCA, CBDA, CBD, CBG or CBC are present in the form of a BDS, and the THCV or CBDV are present in either an isolated form or in the form of a BDS to the patient.

In one embodiment the one or more phytocannabinoids are propyl variant phytocannabinoids.

In a second embodiment the one or more phytocannabinoids are in an acid form.

In a further embodiment the one or more phytocannabinoids are in a neutral or decarboxylated form.

In a preferred embodiment the phytocannabinoid is CBG and is in the form of a BDS.

Preferably the prostate cancer is hormone-sensitive prostate cancer.

In another embodiment the phytocannabinoid is THCVA in an isolated form.

In a further embodiment the prostate cancer is hormone-insensitive prostate cancer and the phytocannabinoid is CBD and is in the form of a BDS or the phytocannabinoid is CBDV and is in the form of a BDS.

Preferably the one or more phytocannabinoids are used in combination or as an adjunct therapy with a chemotherapeutic agent and/or an anti-androgen.

Preferably the chemotherapeutic agent is a mitotic inhibitor. The mitotic inhibitor is preferably from the taxane drug class. More preferably the mitotic inhibitor taken from the taxane drug class is taken from the group: docetaxel; larotaxel; ortataxel; paclitaxel; and tesetaxel.

The one or more phytocannabinoids can be infused in oil or PVA or synthetic hydrogel with polyvinyl alcohol (PVA) having (8%) gel and water (92%), cross-linked by freezing/thawing cycles, and can be used in combination with a chemotherapeutic agent and or anti-androgen the phytocannabinoid is preferably CBG or CBD, which may be in the form of a BDS.

In a further embodiment the one or more phytocannabinoids infused in oil or PVA or PVA can be used for the purpose of slowing down the growth or reducing the volume of a prostate cancer tumour.

The use of one or more propyl phytocannabinoids or acid phytocannabinoids infused in oil or synthetic hydrogel with polyvinyl alcohol (8%) gel and water (92%), cross-linked by freezing/thawing cycles, and can be for use in the down regulation of ERK signalling and effect one or more of: anti-proliferation, anti-metastasis or anti-angiogenesis in a human patient.

The use of one or more propyl phytocannabinoids or acid phytocannabinoids infused in oil or PVA in the manufacture of a medicament to down regulate ERK signalling and effect one or more of: anti-proliferation, anti-metastasis or anti-angiogenesis in a human patient.

A method of treating a patient with cancer comprising administering one or more propyl phytocannabinoids or acid phytocannabinoids infused in oil or PVA to down regulate ERK signalling and effect one or more of: anti-proliferation, anti-metastasis or anti-angiogenesis to the patient.

Preferably the one or more phytocannabinoids are selected from the group consisting of: THCV, CBGV, CBDV, CBGA and CBDA.

Preferably the one or more phytocannabinoids are in an isolated form.

Preferably the one or more propyl or acid phytocannabinoids infused in oil or PVA are for use in the treatment of lung cancer, prostate cancer, or breast cancer.

Preferably the one or more propyl or acid phytocannabinoids infused in oil or PVA are for use in the treatment of bone or lymph metastasis.

The method includes the use of one or more phytocannabinoid acids infused in oil or PVA, excluding CBDA or CBDVA, for use in medicine.

The method includes the use of the one or more phytocannabinoid acids for use in the treatment of cancer.

The use of one or more phytocannabinoid acids infused in oil or PVA is done in the manufacture of a medicament for use in the treatment of cancer.

The method includes treating a patient with cancer comprising administering a therapeutic amount of one or more phytocannabinoid acids infused in oil or PVA to the patient. Preferably the one or more phytocannabinoid acids are in the form of a BDS. Preferably the cancer to be treated is a cancer of the prostate, breast, colon, lung, glioma or skin. Preferably the phytocannabinoid acid is taken from the group consisting of: THCA, CBGA and CBDA. More preferably there is provided a combination of the phytocannabinoid THCA with CBDA and/or CBGA.

The method includes applying an isolated CBD, CBG, CBDV, CBD BDS, CBG BDS and/or CBDV BDS infused in oil or PVA for use in the treatment of a pre-cancerous symptom of colon cancer.

The method includes infusing in oil an isolated CBD, CBG, CBDV, CBD BDS, CBG BDS and/or CBDV BDS infused in oil or PVA in the manufacture of a medicament to treat a pre-cancerous symptom of colon cancer.

The method of treating a patient with a pre-cancerous symptom of colon cancer, comprising administering a therapeutically effective amount of an isolated CBD, CBG, CBDV, CBD BDS, CBG BDS and/or CBDV BDS infused in oil or PVA to the patient.

In one embodiment the isolated CBD, CBG, CBDV, CBD BDS, CBG BDS and/or CBDV BDS infused in oil or PVA are used in the treatment of aberrant crypts in the colon.

In a further embodiment the isolated CBD, CBG, CBDV, CBD BDS, CBG BDS and/or CBDV BDS infused in oil or PVA are used in the treatment of colon polyps.

A combination of phytocannabinoids infused in oil or PVA together with a chemotherapeutic agent which is not a cannabinoid, can be used in the treatment of a glioma.

A combination of phytocannabinoids infused in oil or PVA together with a chemotherapeutic agent which is not a cannabinoid, can be used as a medicament to treat a glioma.

A method of treating a patient with a glioma, includes administering a therapeutically effective amount of a combination of phytocannabinoids infused in oil or PVA together with a chemotherapeutic agent which is not a cannabinoid, to the patient.

Preferably the combination of phytocannabinoids and the chemotherapeutic agent which is not a cannabinoid are packaged for administration separately, simultaneously or sequentially. Preferably the phytocannabinoids are THC and CBD. Preferably the dose level of the phytocannabinoids is sub-effective for the treatment of the glioma if used alone. Preferably the chemotherapeutic agent is temazolamide. Preferably the dose level of the temazolamide is sub-effective for the treatment of glioma if used alone.

The CBD or TCH can be embedded with a slow release agent.

In one embodiment, a time delay barrier can be used. This outer barrier layer of a more hydrophobic substance can be selected from polylactic acid (PLA), polyglycolic acid (PGA), a copolymer of PLA and PGA (PLGA), polycaprolactone (PCL), other biodegradable polyesters, polyamino acids, or other hydrophobic, biodegradable polymers.

Preferably, under the barrier layer and immediately adjacent to the *cannabis* as the therapeutic agent matrix layer another layer is provided that is instead slightly hydrophilic or closer in polarity to the therapeutic agent itself than the outer barrier layer. This middle layer is the key to the rapid, burst characteristic of therapeutic agent elution while the outer barrier layer is the key to the delayed onset characteristic of therapeutic agent elution.

As an alternative or as a complement to providing a separate layer beneath the barrier layer that is opposite in polarity to the barrier layer and closer in polarity to the therapeutic agent, the material used to form the therapeutic agent soluble material can be provided in pockets distributed throughout the barrier layer. By interspersing the barrier matrix with pockets of a hydrophilic substance (i.e. dextran, heparin) a switch effect for accelerated barrier layer degradation and therapeutic agent elution can be better achieved. Upon a threshold level of water penetration into the barrier matrix containing the pockets, the pockets increase in pressure to the point where they burst to destroy the barrier structure. The pockets act as isolated reservoirs or oases for hydrophilic physiologic and other fluids that the barrier layer's base material does not readily accept. Although the biodegradation of the barrier layer may be directed by other means such as the emergence of a restenotic environment in which the barrier layer dissolves, the incorporation of pockets allows additional options for fine-tuning the timing of barrier degradation by also making it indirectly susceptible to hydrophilic fluids and environments.

If the therapeutic agent happens to be hydrophobic rather than hydrophilic the polarities (hydrophobicity and hydrophilicity) of the respective matrices, layers, and/or pockets should be reversed. The bottom line is that the outermost barrier layer is to be opposite in polarity to the therapeutic agent and the inner layer(s) or pocket(s) that are closer to the therapeutic agent are closer in polarity to the therapeutic agent. However, preferably the therapeutic agent itself is contained in a matrix that is opposite in polarity for stabilization. The design is sandwich-like in configuration with the outer barrier and the therapeutic agent matrix analogized to pieces of bread between the unique opposite polarity inner layer or pockets analogized to the meat. The inner opposite polarity layer is the trigger to burst elution because the therapeutic agent easily dissolves within it suddenly and completely.

Under the event triggered approach, there are several ways to trigger the switch to allow therapeutic agent elution to occur upon tissue encapsulation of the CBD or TCH:

1. First, the coating covering the therapeutic agent matrix is designed to immediately break down to allow therapeutic agent elution upon tissue encapsulation. This can be achieved by coating the therapeutic agent matrix with a slightly to hydrophobic, biodegradable outer barrier layer that breaks down quickly upon the presence of a slightly to very hydrophobic environment such as provided by restenotic material. A thin layer of wax or a fatty substance exemplify the type of coating to be used. Specific examples of these include lipoprotein, collagen, polyamino acids, PLA, PLGA, and polycaprolactone, 2. Second, the ECM suppressing therapeutic agent can be bound to a molecule that inactivates the therapeutic agent until ECM factors (i.e. collagen, proteoglycans) are present.

3. Third, the switch can be turned on by other factors accompanying tissue encapsulation or extracellular matrix thickening including: hormones, enzymes, and/or peptides, etc.

4. Fourth, pressure can be used to induce release of the therapeutic agent, i.e. by housing the therapeutic agent within a semi-permeable membrane that bursts or by including pressure-building pockets within a barrier layer.

5. Fifth, pH changes can be used to induce release of the therapeutic agent if the material retaining (i.e. coating or serving as a matrix for) the therapeutic agent is sensitive to acids or bases and degrades (in tissue or in blood) upon being subjected to acidic or basic environments. In one embodiment, the therapeutic agent is coated with a slightly hydrophobic, acid-sensitive layer of PLGA. Tissue encapsulation of the CBD or TCH can trap the PLGA and the acids produced from PLGA degradation. Subsequently, the concentration of acids is dramatically increased which leads to rapid degradation of the PLGA itself.

This event triggered approach offers a high degree of control of therapeutic agent elution and/or activation. The onset of therapeutic agent elution and/or the catalyst for therapeutic agent activation is particularized to occur independently and exclusively on the CBD or TCH localities encapsulated by tissue while the elution is restrained and/or the therapeutic agent remains dormant and inactive on the CBD or TCH localities that are still bare and un-encapsulated. Encapsulation rates vary between procedures, individuals, and CBD or TCH localities. Therefore, event-triggered therapeutic agent control provides an individualized approach for enhanced accuracy, safety and effectiveness.

It is preferred that the dosage of the anti-restenosis therapeutic agent is higher at the ends of the CBD or TCH to compensate more aggressive restenosis at the ends of the CBD or TCH.

In one embodiment, the present invention uses aligned nanofibers and/or aligned nanogrooves to form the CBD or TCH coating to create an artificial functional endothelial layer that will attract the deposition of a natural endothelial layer. The natural endothelial layer is composed of aligned, elongated endothelial cells that will align themselves amongst the aligned fibers and deposit directly on the CBD or TCH itself even when the aligned nanofiber coating is not loaded with any specifically reactive linking agents.

The xenographic/xenogenic artificial functional endothelial layer of aligned fibers and/or aligned grooves may be composed of or seeded with synthetic materials, allogeneic materials (cells or clones from a second subject of the same species as the patient), and/or heterologous materials (cells or clones from a second subject not of the same species as the patient). In any case, the aligned geometry of the artificial functional layer paves the way for the growth of a natural functional layer of autologous endothelial cells produced in vivo that will encapsulate the CBD or TCH CBD or TCHs and injured to tissue to a depth of 0.1 mm thereby masking its xenographic (foreign) nature to preclude an immune response that may cause thrombosis.

One embodiment addresses LST without sacrificing the effectiveness of using restenosis suppressing therapeutic agents to avoid late stage restenosis and using ECM regulating therapeutic agents to reduce thickening of the ECM. This is done by depositing a biodegradable layer of aligned microfibers (AMF), aligned nanofibers (ANF), and/or aligned grooves (AG) on top of a DES as an effective means to delay the onset of release of one or more therapeutic agent (i.e. restenosis or ECM inhibitory therapeutic agents) as well as to facilitate endothelization (see FIG. 2 and FIG. 3). This way the patient benefits from two desired characteristics:

1. the safety of the BMS by having a smooth endothelium or neointima encapsulating the CBD or TCH CBD or TCHs; and 2. the long term effectiveness of proven DES (such as Cypher and Taxus) by maintaining delivery of a local restenosis and/or ECM suppressing therapeutic agent from the CBD or TCH but with a delayed onset.

The AMF/ANF/AG material may take the form of a coating, a matrix, or an CBD or TCH body so long as its structure and orientation are such that it can both facilitate endothelization and also delay the onset of therapeutic agent release, if therapeutic agents are used. Preferably, the AMF/ANF/AG material lasts for 15-30 days before it is fully degraded to expose the therapeutic agent underneath. However, it may work by fully degrading anywhere between 5-60 days. The AMF/ANF/AG material is preferably made of PGA or a copolymer of PGA-PLA. These are proven compounds used on DES as well as biodegradable sutures and are well documented for their compatibility with blood. PGA and PGA-PLA are especially well suited to degrade within 15-30 days. The delay time before onset of release of the ECM suppressing therapeutic agent (i.e. fluoroquinolone, glucosamine, diethylcarbamazine, etc.) is equal to the time it takes the AMF/ANF/AG material to fully degrade. This delay time is controlled by the exact chemical compounds used to create the coating and also the coating thickness. For example, since 50% PLA:50% PGA degrades more quickly than a 75% PLA:25% PGA mix, to obtain the same therapeutic agent release onset delay a thicker layer of 50% PLA:50% PGA would be used than if a 75% PLA:25% PGA mix were used. The AMF/ANF/AG material is preferably between 0.1 micron and 20 microns thick.

Alternatively, instead of PGA and/or PLA, the AMF/ANF/AG material can also preferably be made of poly(ethylene glycol) (PEG), also known as poly(ethylene oxide) (PEO) or polyoxyethylene (POE). Caprolactone (CPL) can also be used. CPL and PEG are elastomeric materials and if the AMF/ANF/AG medical device has elastomeric properties it will better conform to the natural shape of the lumen in which it is inserted or CBD or TCHed. Elastomeric materials are better able to close gaps between a CBD or TCH wall and a lumen wall. Avoiding incomplete apposition of the CBD or TCH CBD or TCHs against the lumen wall reduces the formation of stagnant pockets in which a thrombus is more likely to develop. Metallic CBD or TCH CBD or TCHs are typically stiff and cannot conform well to the lumen when the lumen is not smooth and uniform, as is often the case. However, an elastomeric coating upon non-elastomeric CBD or TCH CBD or TCHs ameliorates this problem by flexing, bending, expanding, and contracting to occupy the differential spaces created by the nonconformity between the lumen wall and the CBD or TCH CBD or TCHs. Alternatively, if the CBD or TCH CBD or TCHs themselves are made of AMF/ANF/AG elastomeric materials they can directly model the irregular surface patterns of anatomic lumens.

The AMF/ANF/AG material can also be made out of biological molecules (biomolecules) such as collagen, fibrin, or fibrinogen. Various other substances that can be used to form the AMF/ANF/AG material are: phosphorylcholine, nitric oxide, high density lipoprotein, polyzene-F, PTFE polyetherester, hydroxyapatite, polyhydroxy-butyrate, polycaprolactone, polyanhydride, poly-ortho ester, polyiminocarbonates, polyamino acids, and polyvinyl alcohol.

Irrespective of the chemical components used to form the AMF/ANF/AG material, when used as a delay coating the AMF/ANF/AG material is preferably negatively charged and also preferably has a nitric oxide functional group. Thus, as the fibers degrade, nitric oxide is released. Within the bloodstream of the lumen occupied by the CBD or TCH, the nitric oxide serves to further inhibit restenosis by preventing platelet aggregation and macrophage/leukocyte infiltration, reducing smooth muscle cell proliferation, and decreasing inflammation generally while aiding the healing process. An aligned coating with a nitric oxide group (ANO) on an CBD or TCH (or other intravascular medical device) forms an artificial endothelium layer due to the smooth, streamlined surface the aligned fibers/grooves provide coupled with the ability of nitric oxide to prevent aberrations on this smooth surface as the fibers degrade.

The inventor recognizes the use of any biocompatible materials that can be formed into aligned nanofibers, aligned microfibers, or aligned grooves for the AMF/ANF/AG material used to form an CBD or TCH, a coating, or a matrix for therapeutic agent(s). The present invention also recognizes the ability to use the AMF/ANF/AG material in conjunction with other coatings, layers, matrices, pores, channels, reservoirs, etc. to delay onset of the release of any therapeutic agent and/or to encourage structured (i.e. aligned) endothelization.

The present invention also teaches the criticality of matching the time period of delay prior to therapeutic agent release with the time it takes for the AMF/ANF/AG CBD or TCH surface to become covered (i.e. encapsulated) by endothelization to a depth of approximately 0.1 mm. The artificial functional endothelium layer itself is a very thin (i.e. only one or a few cells thick). A thin layer does not burden the CBD or TCH with unnecessary volume (i.e. on the periphery of a cross-section) that could make insertion and adjustment within the lumen more difficult. A thin layer also does not significantly reduce the inner diameter of the CBD or TCH's lumen and therefore does not interfere with hemodynamics or obstruct blood supply to a treated area.

When the CBD or TCH is not formed of a material (i.e. such as an elastomeric aligned material) that enables it to conform to the shape of a lumen surface, a thrombus is more likely to develop causing a localized inflammatory reaction. Also, when the CBD or TCH doesn't conform well to the shape of a lumen, the process of restenosis cannot be effectively controlled. Although systematic therapeutic agents administered with BMS and therapeutic agents supplied by DES can slow or modulate the rate of ineffective restenosis they are not typically used to encourage a moderate amount of beneficial restenosis. Any restenosis that does occur in a vessel having an uneven surface with CBD or TCH CBD or TCHs that inadequately conform to the natural cell and protein structure (and/or shape) of the vessel is likely to be uncontrollable and problematic. Smooth muscle cell migration and proliferation is likely to form the first tissue layer over the CBD or TCH CBD or TCHs. In contrast, the present invention provides a pre-formed artificial functional endothelial layer to provoke a first in vivo layer of natural endothelial cell growth.

According to the present invention, an aligned (i.e. AMF/ANF/AG/ANO) coating on the luminal surface aligns both the blood flow and the growth of natural endothelial cell layers in a uniform, optimal direction (i.e. longitudinally along the central axis of the lumen). An aligned inner coating accelerates and optimizes blood flow for better drainage and support. Normal blood flow around the CBD or TCH flushes out immune response agents and toxins, as they are produced, to accelerate drainage and healing. Normal blood flow also feeds the developing, natural endothelial cell layer above the artificial functional endothelial CBD or TCH coating with nutrients.

Once the natural endothelial cell layer has developed to a sufficient extent (i.e. a depth of approximately 0.1 mm) and moderate amounts of beneficial (i.e. aligned) restenosis have been permitted to occur, the result is a camouflaged CBD or TCH buried within normal, healthy tissue. No foreign materials are detectable by the blood and so the blood related immune response and inflammation are inhibited, thereby greatly reducing the risk of thrombosis. As therapeutic agents begin to be eluted from DES upon degradation of the aligned coating, the beneficial, controlled restenosis process ("encapsulation") comes to a halt. The CBD or TCH remains stably buried but the thickness of the luminal walls stops increasing to avoid reclosure. The therapeutic agents are powerful enough to prevent additional encapsulation but cannot undo the beneficial, CBD or TCH-sealing, encapsulation that has already occurred.

Figure 4:
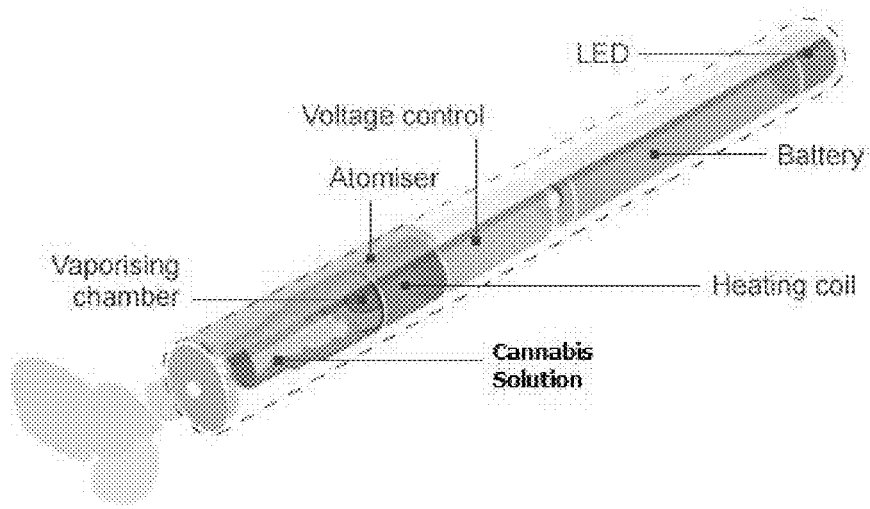
FIG. 4 shows an exemplary e-cigarette for inhaling vapors of *cannabis*.

Elution of the therapeutic ECM suppressing therapeutic agent will arrest the proliferation of neointima (protein deposition) (see FIG. 4). Due to the delay in the onset of therapeutic agent release, by the time the therapeutic agents are released all the CBD or TCH CBD or TCHs are encapsulated with endothelium and/or smooth muscle. Therefore, higher dosages of therapeutic agents, faster elution rates, and/or more aggressive therapeutic agents can be used to ensure maximum effectiveness in preventing restenosis and inhibiting excessive ECM thickening in the long term without fear of LST from an immune reaction. Once the CBD or TCH CBD or TCHs are smoothly buried beneath a thin natural tissue layer thrombosis is unlikely.

Optionally, the CBD or TCH may have semi-permeable cross-sectional side walls extending through the surface area of the cross section on each end adjacent to a target site to be treated with an eluted therapeutic agent. The side walls would serve as barriers to the therapeutic agent to concentrate it at the target site and avoid the negative effects of systematic therapeutic agent distribution. Such sidewalls would also conserve the therapeutic agent to be maintained where it is needed most to allow less total therapeutic agent within the CBD or TCH to be equally effective by reducing the washout effect. Reducing the total therapeutic agent stored in the state (while maintaining effectiveness) is beneficial because then the CBD or TCH walls can be thinner and it is also less expensive. The semi-permeable nature of the side walls allows them to permit the influx of important nutrients needed at the constricted vessel site and to permit the out flux of waste thus preserving hemodynamics. The cross-sectional side walls would dissolve naturally in time to correspond with the termination of the desired therapeutic agent treatment period.

Optionally, the CBD or TCH may include radio-opaque substances in one or more of the materials of which it is formed or in one or more coatings. An array of different, distinguishable radio-opaque substances may also be used in each layer or coating. These substances would enable a physician to externally observe the placement, progress, and improvement of the CBD or TCHing procedure without causing the patient discomfort from an internal inspection and without risking displacing the CBD or TCH during an internal (i.e. endoscopic) inspection.

Another approach to avoiding LST while still controlling restenosis is by accelerating the endothelization of the CBD or TCH through aligned scaffolding without the antirestenosis therapeutic agent. The bare CBD or TCH can be made of (at least in part) or coated with elongated AMF/ANF/AG/ANO aligned with the direction of blood flow (i.e. long axis of fibers parallel to the direction of blood flow). Endothelial cells (ECs) are themselves elongated and tend to also be aligned with the direction of blood flow. By aligning the fibers with the preferred alignment of ECs, the deposition of ECs over the CBD or TCH (including but not limited to the CBD or TCH CBD or TCHs) is accelerated (aligned scaffolding). The presence of ECs tends to arrest the restenosis process (smooth muscle proliferation). The AMF/ANF/AG/ANO are preferably laid down on the inner diameter (ID) of the CBD or TCH (see FIG. 3). The outer diameter (OD) or abluminal surface of the CBD or TCH is typically embedded in or aligned against the luminal surface of the vessel so that the longitudinal alignment of the fibers here is not as important as for the inner diameter or luminal surface of the CBD or TCH.

The CBD or TCH CBD or TCHs are typically 50 to 100 microns wide. The fibers are preferably 0.5 to 10 microns wide. Therefore, regardless of the CBD or TCH CBD or TCH orientation, the fibers can have an aspect ratio of 5 or greater. By having an aspect ratio greater than 2, the fibers can provide effective longitudinally aligned scaffolding for ECs to grow on.

The AMF/ANF/AG/ANO coating or surface can be impregnated or coated with antiplatelet or anticoagulant therapeutic agents such as heparin, ticlopidine, chlopidrel, enoxaparin, dalteparin, hirudin, dextran, bivalirudin, argatroban, danparoid, Tissue Factor Pathway Inhibitor (TFPI), GPVI antagonists, antagonists to the platelet adhesion receptor (GP1b-V-IX), antagonists to the platelet aggregation receptor (GPIIb-IIIa) or any combination of the aforementioned agents.

The AMF/ANF/AG/ANO material can also be impregnated with endothelization promoting substances such as vascular endothelial growth factor (VEGF), angiopoietin-1, antibodies to CD34 receptors, and/or hirudin, dextran.

The coating can be applied to the inner diameter (ID) of the CBD or TCH in the form of longitudinally aligned microfibers, nanofibers, grooves, or nitric oxide carrying elements by several modified processes of electrospinning:

1A. Aligned Nanofibers on CBD or TCH CBD or TCHs only: A dispensing syringe is loaded with a solution of the fiber material and is charged (i.e. positive) with a high voltage (>1 kV) to charge the solution. The CBD or TCH is either grounded or charged by applying the opposite voltage (i.e. negative). The outer diameter (OD) of the CBD or TCH is covered with a polar or conductive tube that sticks to the fiber material well. For example, if PGA or PLA are used as the polymer solution from which the fiber material is formed, polyethylene terephthalate (PET) is heat shrunk on the OD of the CBD or TCH. The CBD or TCH is held by a grounded or charged (i.e. negative) collet on the OD of one end. The dispensing syringe needle with a 90 degrees bend (or side hole) at the tip is inserted inside the ID of the CBD or TCH from the open end of the CBD or TCH. The charged solution is dispensed from the needle tip onto the CBD or TCH ID as longitudinally aligned micro/nanofibers/grooves/nitric-oxide carrying elements as the syringe tip is moved back and forth longitudinally. As the syringe tip completes one pass from one end to the other, the collet is indexed (turned incrementally) to lay down the adjacent fiber. This process continues until the whole CBD or TCH ID is covered with aligned fibers, grooves or elements. Once the coating is finished, the cover (i.e. polar or conductive tube such as PET) on the OD can be peeled off to clear the CBD or TCH openings of fibers.

1B. Aligned Nanofibers covering all CBD or TCH: A dispensing syringe is loaded with a solution of the fiber material and is charged (i.e. positive) with a high voltage (>1 kV) to charge the solution. The CBD or TCH is either grounded or charged by applying the opposite voltage (i.e. negative). The CBD or TCH is held by a grounded or charged (i.e. negative) collet on the OD of one end. The dispensing syringe needle with a 90 degrees bend (or side hole) at the tip is inserted inside the ID of the CBD or TCH from the open end of the CBD or TCH. The charged solution is dispensed from the needle tip onto the CBD or TCH ID as longitudinally aligned micro/nanofibers/grooves/nitric-oxide carrying elements as the syringe tip is moved back and forth longitudinally. As the syringe tip completes one pass from one end to the other, the collet is indexed (turned incrementally) to lay down the adjacent fiber. This process continues until the whole CBD or TCH ID is covered with aligned fibers, grooves or elements.

2. The highly charged (i.e. +10 kV) syringe as described above is fixed longitudinally. The CBD or TCH is grounded. A ring of opposite charge (i.e. −10 kV) is placed near the CBD or TCH. The dispensing syringe is pulsed by pulsing syringe pressure, a needle valve, or charging to completely dispense one aligned fiber. The CBD or TCH is then rotationally indexed for the next pulsed dispensing.

3. A hollow ring containing the solution of fiber material has series of micro/nano-holes on the end for dispensing parallel fibers arranged in a diameter close to the diameter of the CBD or TCH. The ring is highly charged (i.e. +10 kV) to charge the fiber material in solution. The CBD or TCH is grounded. A ring close to the diameter of the CBD or TCH is charged with an opposite charge (i.e. −10 kV) on the opposite end of the CBD or TCH. This charged state will cause the solution which forms the fibers to eject from the holes in parallel, longitudinally towards the oppositely charged ring while simultaneously adhering to the CBD or TCH along the path from one ring to another.

In another embodiment, the inner surface of the CBD or TCH CBD or TCH can have micro/nano-grooves etched on it longitudinally (parallel to axis of CBD or TCH). ECs will tend to grow into these grooves. The grooves are preferably 1 to 10 microns wide. In the same manner, the grooves can also be ridges or channels. The longitudinally aligned micro/nano-grooves may also be used as reservoirs or longitudinal wells for storing therapeutic agents within the aligned fiber layers for controlled or multi-phase elution.

These AMF/ANF/AG/ANO CBD or TCHs are particularly advantageous when applied to intravascular bifurcations or vessels with one or more corollary branch adjacent to a main lumen. Bifurcated vessels tend to have much higher rates of restenosis with both conventional BMS and DES than do non-bifurcated vessels.

The present invention controls tissue encapsulation of the CBD or TCH and of injured tissue in at least three ways: biologically, geometrically, and chronologically.

Biologically, aligned nano/microfibers with or without aligned nano/microgrooves therein (or alternatively, aligned grooves formed within a non-fibrous material) facilitate functional endothelization by encouraging a uniform orientation in any cell growth that occurs (whether of true endothelial cells or artificial endothelial cells). The polymers or other materials chosen for the construction of the nano/microfibers or nano/microgrooves must be biocompatible to permit the natural flow of blood and other bodily fluids through the lumen adjacent the CBD or TCH's inner surface without elicitation of an immune response or thrombosis. The materials used to form the fibers or the material within which the grooves are etched can be synthetic or naturally derived. Suitable materials include: biodegradable materials such as polyglycolic acid (PGA), polylactic acid (PLA), copolymer of PLA and PGA (PLGA), hydroxyapatite (HA), polyetherester, polyhydroxybutyrate, polyvalerate, polycaprolactone, polyanhydride, poly-ortho ester, polyiminocarbonates, polyamino acids, polyethylene glycol, polyethylene oxide, and polyvinyl alcohol; non-biodegradable polymers such as fluoropolymer like Polytetrafluoroethylene (PTFE), polyzene-F, polycarbonate, carbon fiber, nylon, polyimide, Polyether ether ketone, polymethylmethacrylate, polybutylmethacrylate, polyethylene, polyolefin, silicone, and polyester; biological substances such as high density lipoprotein, collagen, fibrin, phosphorylcholine (PC), gelatin, dextran, or fibrinogen.

Geometrically, the invention is designed to only allow 0.1 mm thickness of encapsulation (of CBD or TCH CBD or TCHs or the entire CBD or TCH body and of injured tissue) before the therapeutic agent elution process begins to inhibit further encapsulation. Another aspect of geometric control is the alignment of fibers/grooves and all growth thereupon whether it be endothelial cells, smooth muscle cells, proteins, matrix fibers, or collagen fibers. Due to the structure supplied by the fibers/grooves, all subsequent in vivo growth, migration, and/or proliferation is necessarily aligned to correspond to the template set by the fibers/grooves. Aligned growth does not interfere with blood flow. Further, even if the initial natural layers of biologically derived materials deposited are not the ideal materials (i.e. smooth muscle cells instead of endothelial cells), as long as they are aligned they are suspected not to impede the deposition of the optimal materials when they come along.

Chronologically, the invention assures that the complete degradation of the polymer (or other material) layer serving as a delay coat for the antiproliferative therapeutic agent corresponds to the time when an optimal amount (i.e. 0.1 mm thickness) of encapsulation has occurred because that point in time also marks the onset of elution of the antiproliferative therapeutic agent which will suppress further thickening of tissue encapsulation. Temporal control over the elution of the antiproliferative and/or other therapeutic agents may also be achieved by an external activation means that signals for the aligned therapeutic agent reservoirs to begin elution. The external activation means may be electromagnetic radiation, infrared light, microwave radiation, x-ray radiation, etc. This type of external activation means would provide very precise control of the onset of therapeutic agent elution. Since the rate of encapsulation will vary from individual to individual and from procedure to procedure depending upon a multitude of factors, a pre-elution assessment (i.e. imaging for endothelial cell markers) of the extent of encapsulation can precede initiation of the external activation means to ensure elution does not begin prematurely.

In some embodiments, the teachings are directed to a therapeutic coating that promotes formation of a functional endothelium on a medical device. In these embodiments, the coating comprises a biodegradable drug-containing layer that is positioned over a surface of a medical device and serves as a source of a drug that functions as an anti-proliferative agent in a subject. The coating also comprises a biodegradable drug-reservoir layer positioned over a surface of the drug-containing layer. The drug-reservoir layer comprises a drug-retaining layer, wherein the drug-retaining layer is void or substantially void of the drug at a time of implantation in the subject and functions to retain and at least substantially block an initial release of the drug into the subject for a time sufficient to form a functional endothelium over the surface of the medical device. In these embodiments, the functional endothelium can provide a source of thrombomodulin to the subject. It should be appreciated that the drug may be at least substantially miscible in the drug-reservoir layer to facilitate a retention of the drug. It should be appreciated that the time sufficient to form a functional endothelium may vary according to selection of subject, medical device, location of an CBD or TCH, materials used, and the like. In some embodiments, the time can be at least about 20 days.

In some embodiments, the drug-containing layer can comprise a poly(lactic-co-glycolic acid), a monomer ratio of lactic acid to glycolic acid ranges from about 85:15 to about 50:50, and a molecular weight ranging from about 90 KDaltons to about 160 KDaltons. And, in some embodiments, the drug-retaining layer can comprise a poly(lactic-co-glycolic acid) having ester terminal groups, a monomer ratio of lactic acid to glycolic acid ranging from about 85:15 to about 50:50, and a molecular weight ranging from about 90 KDaltons to about 160 KDaltons.

Moreover, the drug-retaining layer can comprise a polymer having ester-terminal groups. The polymer can have, for example, a molecular weight ranging from about 50 KDaltons to about 190 KDaltons, and a structure that remains at least substantially undegraded during the initial release of the drug, the structure comprising P—CO2R, where P is the polymer backbone and R is an alkyl group having from 1 to 4 carbons.

The coating may at least substantially promote development of the functional endothelium as the source of the thrombomodulin when compared to a control development of such endothelium formation observed following CBD or TCHation of a metal or polymer drug-eluting medical device. In addition, the coating may at least substantially inhibit development of a hyperproliferative tissue when compared to a control development of such hyperproliferative tissue observed following CBD or TCHation of a metal or polymer medical device that does not elute a drug. In some embodiments, the medical device comprises a CBD or TCH.

The coatings can be designed for a delay time before onset of the release of the drug and elution of the drug at a certain rate. In some embodiments, the drug-reservoir layer can further comprise an accelerant layer to accelerate the onset of elution. And, in some embodiments, the accelerant layer having a poly(lactic-co-glycolic acid) with acid terminal groups, a monomer ratio of lactic acid to glycolic acid that ranges from about 85:15 to about 50:50, and a molecular weight that ranges from about 90 KDaltons to about 120 KDaltons. In some embodiments, the accelerant layer can comprise a drug. The amount of drug in the accelerant layer can be 0, 5, 10, 15, 20, 25, 30, 35, 40, 45, 50, 60 percent, or any amount therein.

In fact, other variables can be used to design for a desired delay time and release rate of the drug. In some embodiments, for example, the thickness ratio of the drug-reservoir layer to the drug-containing layer can range from about 4:1 to about 10:1, and the miscibility of the drug in a coating can be preselected to affect the rate of drug migration. In some embodiments, the thickness of the coating can range from about 2 microns to about 9 microns. And, in some embodiments, the thickness ratio of the drug-retaining layer to the drug-containing layer ranges from about 4:1 to about 7:1.

As such, the teachings are generally directed to a method of inhibiting the formation of hyperproliferative tissue and promoting the formation of a functional endothelium after implantation of a medical device in a subject. The method can comprise applying a therapeutic coating on a medical device and CBD or TCHing the device in the subject. In some embodiments, the coating can comprise a biodegradable drug-containing layer that (i) is positioned over a surface of a medical device and (ii) serves as a source of a drug that functions as an anti-proliferative agent in a subject; and, a biodegradable drug-reservoir layer positioned over a surface of the drug-containing layer and comprising a drug-retaining layer, the drug-retaining layer remaining void or substantially void of the drug at a time of implantation in the subject and functioning to retain and at least substantially block an initial release of the drug into the subject for a time sufficient to form a functional endothelium over the surface of the medical device, the functional endothelium providing a source of thrombomodulin to the subject.

In some embodiments, the drug-containing layer can be applied as a solvent mixture and the solvent can be dried after application using a substantially non-reactive heated gas. The drying can serve to at least substantially inhibit mobilization of the drug from the drug-containing layer during application of additional layers in the formation of the coating. In some embodiments, the drug-reservoir layer can comprise at least one sub-layer having a thickness of less than or equal to 3 microns, where a repeated application of the sub-layer can be used to form thicknesses of greater than 3 microns. In some embodiments, the accelerant layer can be positioned between the drug-containing layer and the remainder of the drug-reservoir layer, is more hydrophilic than the remainder of the drug-reservoir layer, and comprises at least one sub-layer having a thickness of less than or equal to 3 microns, where a repeated application the sub-layer is used to form thicknesses of greater than 3 microns. The application of the sub-layers can be used to at least substantially promote a retention of the drug in the drug-containing layer during formation of the coating when compared to such a coating without the application of the sub-layers.

The coatings taught herein can, in some embodiments, further comprise pockets of hydrophilic material in the drug-retaining layer, wherein the hydrophilic material comprises a component selected from the group consisting of dextran, heparin, ticlopidine, chlopidogrel, enoxaparin, dalteparin, hirudin, bivalirudin, argatroban, and danparoid. And, in some embodiments, the drug can be selected from the group consisting of fluoroquinolone, paclitaxel, rapamycin, sirolimus, everolimus, biolimus, zotarolimus, tacrolimus, fibroblast growth factor (bFGF), rapamycin analogs, antisense dexamethasone, angiopeptin, BATIMISTAT, tranilast, transilast, halofuginon, acetylsalicylic acid, hirudin, steroids, ibuprofen, antimicrobials, antibiotics, actinomycin D, tissue plasma activators, estradiol, and transcription factor E2F1.

It should be appreciated that, in the embodiments taught herein, the drug may be selected by its miscibility in a preselected polymer matrix. For example, the drug may be selected because it is at least substantially miscible in the drug-reservoir layer in order to retain the drug for a desired amount of time. Or, the drug may be miscible to a preselected degree, an amount sufficient to facilitate a desired retention time of the drug. A desired retention time is facilitated, for example, in a case where a functional endothelium has formed to a desired extent. It should be appreciated that the desired retention time is facilitated where the retention time is modulated to a desired amount, and the modulation of the time can include an increase or a decrease in the retention time through altering one or more coating variables, as described herein. One of skill should appreciate, for example, that miscibility of the drug with the polymer is a variable that can modulate an affinity of the drug for the polymer, in some embodiments, thus affecting retention time.

In some embodiments, the drug and polymer are mixed or blended in solution, and one skill will appreciate that the mixes or blends can be considered substantially miscible, for example, where they mix or blend homogeneously in the desired proportions of drug to polymer, at least for the purposes of the teachings provided herein. In contrast, the mixes or blends may be considered immiscible, at least for the purposes of the teachings provided herein, where the mix or blend of polymer and drug is not homogeneous in the mix or blend in the proportions desired. In some embodiments, a drug can be considered substantially miscible in a polymer, where a homogeneous, saturated solution comprising the drug in a solvent spreads on a layer of the polymer, such that (i) the solution of the drug in the solvent has a contact angle of greater than 90 degrees on the surface of the polymer; and (ii) the layer of the polymer was formed used the same solvent. In some embodiments, the drug is substantially miscible in the polymer where the surface tension of the drug and the surface tension of the polymer are the same or similar when compared using the same solvent. A surface tension is the same, where the difference is not statistically significant, and similar, where the surface tension does not vary by more than 1, 2, 3, 4, 5, 10, 15, 20, 25, or 30 percent, in some embodiments. It should be appreciated, however, that any method known to one of skill can be used to determine the relative degree of miscibility and affinity between the drug and the polymer.

In some embodiments, the retention time of a drug can be a time sufficient amount, or an otherwise desired amount of time, chosen based on any number of parameters recognized and known to one of skill in the art of drug elution from CBD or TCHed medical devices. Such parameters can vary the desired amount of time based on, for example, type of CBD or TCH, location of CBD or TCH, construction of CBD or TCH, selection of drug, desired effect, and the like.

It should be appreciated that the "time sufficient to form a functional endothelium" may vary according to selection of subject, medical device, location of a CBD or TCH, materials used, and the like. In some embodiments, the time can be at least about 20 days. In some embodiments, a sufficient amount of time can range from about 5 days to about 120 days, from about 10 days to about 90 days, from about 12 days to about 50 days, from about 14 days to about 45 days, from about 15 days to about 90 days, from about 20 days to about 60 days from about 25 days to about 45 days, from about 20 days to about 40 days, from about 20 days to about 30 days, from about 25 days to about 35 days, or any range therein.

The polymeric compositions taught herein include any desired polymer, combination of polymers, copolymers and agents known to one of skill to be useful as a medical device, or coating, as taught herein. These polymers can be biodegradable due to their labile nature, such as the labile nature of the ester groups that are present in some polymers. In some embodiments, these compositions can be designed such that they can be broken down, absorbed, resorbed and eliminated by a mammal. As such, the compositions can be used, for example, to form medical articles and coatings.

The terms "combine," "combined," and "combining" all refer to a relationship between components of a composition and include blends, mixtures, linkages, and combinations thereof, of components that form the compositions. The linkages can be connections that are physical, chemical, or a combination thereof. Examples of physical connections include, but are not limited to, an interlinking of components that can occur, for example, in interpenetrating networks and chain entanglement. Examples of chemical connections include, but are not limited to, covalent and noncovalent bonds. Covalent bonds include, but are not limited to, simple covalent bonds and coordinate bonds. Non-covalent bonds include, but are not limited to, ionic bonds, and intermolecular attractions such as, for example, hydrogen bonds and attractions created by induced and permanent dipole-dipole interactions.

Compositions that are selected for an in vivo use should meet particular requirements with regard to physical, mechanical, chemical, and biological properties of the compositions. An example of a physical property that can affect the performance of a biodegradable composition in vivo is water uptake. An example of a mechanical property that can affect the performance of a composition in vivo is the ability of the composition to withstand stresses that can cause mechanical failure of the composition such as, for example, cracking, flaking, peeling, and fracturing. An example of a chemical property that can affect performance of a biodegradable composition in vivo is the rate of absorption of the composition by a subject. An example of a biological property that can affect performance of a composition in vivo is the bioactive and/or bio beneficial nature of the composition, While not intending to be bound by any theory or mechanism of action, water uptake by a composition can be an important characteristic in the design of a composition. Water can act as a plasticizer for modifying the mechanical properties of the composition. Control of water uptake can also provide some control over the hydrolysis of a coating and thus can provide control over the degradation rate, absorption rate, and the agent release rate of a medical article or coating in vivo, such as for the release of a drug. In some embodiments, an increase in hydrolysis can also increase the release rate of an agent by creating channels within a medical article or coating that can serve as transport pathways for diffusion of the agents from the composition. The terms "subject" and "patient" can be used interchangeably and refer to an animal such as a mammal including, but not limited to, non-primates such as, for example, a cow, pig, horse, cat, dog, rat, and mouse; and primates such as, for example, a monkey, or a human.

In some embodiments, the compositions may be used, for example, to form medical articles and coatings (i) that have sufficient mechanical properties for applications that can benefit from biodegradable polymers, (ii) that can release agents substantially free of additional molecules derived from a polymeric carrier, (iii) that can be designed to have a predetermined release rate and absorption rate; and (iv)

that can be combined with agents that are not only bioactive and/or bio beneficial but also control a physical property and/or a mechanical property of a medical article or coating formed from the polymer.

A polymer or coating can be "biodegradable," for example, when it is capable of being completely or substantially degraded or eroded when exposed to an in vivo environment or a representative in vitro environment. A polymer or coating is capable of being degraded or eroded when it can be gradually broken-down, resorbed, absorbed and/or eliminated by, for example, hydrolysis, enzymolysis, oxidation, metabolic processes, bulk or surface erosion, and the like within a subject. It should be appreciated that traces or residue of polymer may remain on the device, near the site of the device, or near the site of a biodegradable device, following biodegradation. The terms "bioabsorbable" and "biodegradable" are used interchangeably in this application. The polymers used in the teachings herein may be biodegradable and may include, but are not limited to, condensation copolymers. In some embodiments, the drug-containing layer can comprise a poly(lactic-co-glycolic acid), a monomer ratio of lactic acid to glycolic acid ranges from about 85:15 to about 50:50, and a molecular weight ranging from about 90 KDaltons to about 160 KDaltons.

Biodegradable polymers can be used, and biodegradable polymers should be selected according to their behavior and hydrolysis in vivo. In some embodiments, the number average molecular weight of the polymer fragments should be at or below about 40,000 Daltons, or any range therein. In some embodiments, the molecular weight of the fragments range from about 300 Daltons to about 40,000 Daltons, from about 8,000 Daltons to about 30,000 Daltons, from about 10,000 Daltons to about 20,000 Daltons, or any range therein. The molecular weights are taught herein as a number average molecular weight.

Examples of polymers that can be used in some embodiments include, but are not limited to, poly(acrylates) such as poly(butyl methacrylate), poly(ethyl methacrylate), poly(hydroxylethyl methacrylate), poly(ethyl methacrylate-co-butyl methacrylate), copolymers of ethylene-methyl methacrylate; poly(2-acrylamido-2-methylpropane sulfonic acid), and polymers and copolymers of aminopropyl methacrylamide; poly(cyanoacrylates); poly(carboxylic acids); poly(vinyl alcohols); poly(maleic anhydride) and copolymers of maleic anhydride; fluorinated polymers or copolymers such as poly(vinylidene fluoride), poly(vinylidene fluoride-co-hexafluoro propene), poly(tetrafluoroethylene), and expanded poly(tetrafluoroethylene); poly(sulfone); poly(N-vinyl pyrrolidone); poly(aminocarbonates); poly(iminocarbonates); poly(anhydride-co-imides), poly(hydroxyvalerate); poly(L-lactic acid); poly(L-lactide); poly(caprolactones); poly(lactide-co-glycolide); poly(hydroxybutyrates); poly(hydroxybutyrate-co-valerate); poly(dioxanones); poly(orthoesters); poly(anhydrides); poly(glycolic acid); poly(glycolide); poly(D,L-lactic acid); poly(D,L-lactide); poly(glycolic acid-co-trimethylene carbonate); poly(phosphoesters); poly(phosphoester urethane); poly(trimethylene carbonate); poly(iminocarbonate); poly(ethylene); poly(propylene) co-poly(ether-esters) such as, for example, poly(dioxanone) and poly(ethylene oxide)/poly(lactic acid); poly(anhydrides), poly(alkylene oxalates); poly(phosphazenes); poly(urethanes); silicones; poly(esters); poly(olefins); copolymers of poly(isobutylene); copolymers of ethylene-alphaolefin; vinyl halide polymers and copolymers such as poly(vinyl chloride); poly(vinyl ethers) such as poly(vinyl methyl ether); poly(vinylidene halides) such as, for example, poly(vinylidene chloride); poly(acrylonitrile); poly(vinyl ketones); poly(vinyl aromatics) such as poly(styrene); poly(vinyl esters) such as poly(vinyl acetate); copolymers of vinyl monomers and olefins such as poly(ethylene-co-vinyl alcohol) (EVAL), copolymers of acrylonitrile-styrene, ABS resins, and copolymers of ethylene-vinyl acetate; poly(amides) such as Nylon 66 and poly(caprolactam); alkyd resins; poly(carbonates); poly(oxymethylenes); poly(imides); poly(ester amides); poly(ethers) including poly(alkylene glycols) such as, for example, poly(ethylene glycol) and poly(propylene glycol); epoxy resins; polyurethanes; rayon; rayon-triacetate; biomolecules such as, for example, fibrin, fibrinogen, starch, poly(amino acids); peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and derivatives, analogs, homologues, congeners, salts, copolymers and combinations thereof. In some embodiments, other polymers may be selected such that they specifically exclude any one or any combination of these polymers.

In some embodiments, the coatings can comprise one or more biodegradable polymers. Examples of biodegradable polymers include, but are not limited to, polymers having repeating units such as, for example, an α-hydroxycarboxylic acid, a cyclic diester of an α-hydroxycarboxylic acid, a dioxanone, a lactone, a cyclic carbonate, a cyclic oxalate, an epoxide, a glycol, an anhydride, a lactic acid, a glycolic acid, a lactide, a glycolide, an ethylene oxide, an ethylene glycol, or combinations thereof. In some embodiments, the biodegradable polymers include, but are not limited to, polyesters, poly(ester amides); amino acids; PEG and/or alcohol groups, polycaprolactones, poly(L-lactide), poly(D,L-lactide), poly(D,L-lactide-co-PEG) block copolymers, poly(D,L-lactide-co-trimethylene carbonate), polyglycolides, poly(lactide-co-glycolide), polydioxanones, polyorthoesters, polyanhydrides, poly(glycolic acid-co-trimethylene carbonate), polyphosphoesters, polyphosphoester urethanes, poly(amino acids), polycyanoacrylates, poly(trimethylene carbonate), poly(imino carbonate), polycarbonates, polyurethanes, copoly(ether-esters) (e.g. PEO/PLA), polyalkylene oxalates, polyphosphazenes, PHA-PEG, and any derivatives, analogs, homologues, salts, copolymers and combinations thereof. In some embodiments, the polymers can include poly(glycerol sebacate); tyrosine-derived polycarbonates containing desaminotyrosyl-tyrosine alkyl esters such as, for example, desaminotyrosyl-tyrosine ethyl ester (poly(DTE carbonate)); and any derivatives, analogs, homologues, salts, copolymers and combinations thereof. In some embodiments, the polymers are selected such that they specifically exclude any one or any combination of these polymers.

In some embodiments, the polymers can be chemically connected by covalent bonds. In some embodiments, the polymers can be chemically connected to by non-covalent bonds such as, for example, by ionic bonds, inter-molecular attractions, or a combination thereof. In some embodiments, the polymers can be physically connected. In some embodiments, the polymers can be chemically and physically connected. Examples of ionic bonding can include, but are not limited to, ionic bonding of an anionic site to a cationic site between polymers. In some embodiments, an anionic site can be bound to a quaternary amine. Examples of inter-molecular attractions include, but are not limited to, hydrogen bonding such as, for example, the permanent dipole interactions between hydroxyl, amino, carboxyl, amide, and sulfhydryl groups, and combinations thereof. Examples of physical connections can include, but are not limited to, interpenetrating networks and chain entanglement. The polymers can also be blended or mixed.

The behavior of the polymer matrix can be changed through selection of any number of factors that provide the desired drug elution, chemical and physical characteristics of the coatings taught herein. For example, the terminal end groups can be designed to contribute to imparting such characteristics in the polymers. A more hydrophilic end-group can increase the rate of ingress of water, for example, and likewise increase the rate of hydrolysis of the polymer chains, at least in some embodiments. Likewise, a less hydrophilic group can deter in the ingress of water, and slow the rate of hydrolysis, at least in some embodiments.

It should be appreciated that a polymer can be selected to have acid terminal end-groups, hydroxyl terminal end-groups, alkyl-ester end-groups, or a combination thereof. Moreover, a polymer layer can be created using sub-layers, where the layer can have a sub-layer having acid groups, a sub-layer having hydroxyl groups, a sub-layer having ester end-groups, or a combination thereof. In fact, the construction of the layers and sub-layers can be designed based on thickness ratios to design a coating that provides a desired characteristic or set of characteristics including, but not limited to, drug-retention time, a desired rate of hydrolysis, a desired glass transition temperature, a desired drug-elution rate, a desired toughness, a desired elasticity, a desired modulus, or a combination thereof.

Molecular weights can also be selected for the polymer in a particular layer or set of layers in the coating, as a mixture of molecular weights in a particular layer or set of layers, or as a set of sub-layers, where each layer in the sub-layer can have an independently selected molecular weight, mixture of molecular weights, or a combination thereof, where the molecular weight or mixture of molecular weights can be the same or different for each sub-layer. And, in many embodiments, a desired characteristic is that the polymers have a structure that remains at least substantially undegraded during the initial release of the drug. In some embodiments, for example, the drug-retaining layer can comprise a polymer having ester-terminal groups.

In some embodiments, the drug-retaining layer can comprise a poly(lactic-co-glycolic acid) having ester terminal groups, a monomer ratio of lactic acid to glycolic acid ranging from about 85:15 to about 50:50, and a molecular weight ranging from about 90 KDaltons to about 160 KDaltons.

The molecular weights can be selected and tailored for a particular polymer selection and for a particular coating layer and purpose. For example, the polymer can have a molecular weight ranging from about 50 KDaltons to about 190 KDaltons, from about 50 KDaltons to about 190 KDaltons, from about 50 KDaltons to about 180 KDaltons, from about 60 KDaltons to about 170 KDaltons, from about 70 KDaltons to about 160 KDaltons, from about 80 KDaltons to about 150 KDaltons, from about 90 KDaltons to about 140 KDaltons, from about 90 KDaltons to about 160 KDaltons, from about 100 KDaltons to about 160 KDaltons, or any range therein.

Without intending to be bound by any theory or mechanism of action, in some embodiments, the drug-reservoir layer is initially implanted in a "drug-absorbing" state and is later transformed into a "drug-release" state over time due to changes in the physical and chemical structure across the coating in vivo. In the drug-absorbing state, the drug-reservoir layer has the highest affinity for the drug. In the drug-release state the drug-reservoir layer has a substantially lower affinity for the drug. The drug can have the highest solubility in the drug-reservoir layer in the drug-absorbing state and in the drug-release state, the drug can have a substantially lower solubility in the drug-reservoir layer. In some embodiments, the drug-absorbing state can reflect the state in which the glass transition temperature (Tg) of the drug-reservoir layer is higher than the temperature of the surrounding tissue/fluid, and the drug-release state can reflect the state at which the Tg of drug-reservoir layer is equal to or less than that of surrounding tissue/fluid. In some embodiments, coating has a Tg above the surrounding tissue temperature of 37 degrees C.

The polymer end-groups can have any structure known to one of skill that will provide the desired polymer characteristics for a particular coating layer or set of layers. In some embodiments, the end-group can be an ester-terminal group. For example, the polymer structure can comprise P—CO2R, where P is the polymer backbone and R can be an alkyl group having from 1 to 4 carbons, from 1 to 20 carbons, from 2 to 12 carbons, from 1 to 10, from 2 to 8, from 1 to 6 carbons, from 1 to 5 carbons, or any range therein. In some embodiments, R can be any end-group known to one of skill, with the limitation that R cannot affect usefulness of the polymer, for example, the ability of the polymer to be applied as a coating on a desired medical device. In some embodiments, R can be saturated, unsaturated, aromatic, aliphatic, or any combination thereof.

In some embodiments, an R group can be a H; an aliphatic hydrocarbon group such as, for example, an alkyl, alkenyl, or alkynyl group; an aromatic group such as, for example, an aryl, aralkyl, aralkenyl, of aralkynyl group; various other groups as defined herein, or a combination thereof.

In some embodiments, the aliphatic radicals have from about 1 to about 50 carbon atoms, from about 2 to about 40 carbon atoms, from about 3 to about 30 carbon atoms, from about 4 to about 20 carbon atoms, from about 5 to about 15 carbon atoms, from about 6 to about 10 carbon atoms, and any range therein. In some embodiments, the aromatic radicals have from about 4 to about 200 carbon atoms, from about 6 to about 150 carbon atoms, from about 12 to about 120 carbon atoms, from about 18 to about 90 carbon atoms, from about 24 to about 60 carbon atoms, and any range therein.

The term "alkyl" refers to a straight-chained or branched hydrocarbon chain. Examples of alkyl groups include lower alkyl groups such as, for example, methyl, ethyl, n-propyl, iso-propyl, n-butyl, iso-butyl, t-butyl or iso-hexyl; upper alkyl groups such as for example, n-heptyl, n-octyl, isooctyl, nonyl, decyl, and the like; lower alkylene such as, for example, ethylene, propylene, propylyne, butylenes, butadiene, pentene, n-hexene and iso-hexene; and upper alkylene such as, for example, n-heptene, n-octene, iso-octene, nonene, decene, and the like. Persons of ordinary skill in the art are familiar with numerous straight-chained and branched alkyl groups, which are within the scope of the present invention. In addition, such alkyl groups may also contain various substituents in which one or more hydrogen atoms is replaced by a functional group, or the alkyl groups can contain an in-chain functional group. The phrase "straight-chained or branched" includes any substituted or unsubstituted acyclic carbon-containing compounds including, but not limited to, alkanes, alkenes and alkynes.

The term "alkenyl" refers to a straight-chained or branched hydrocarbon chain including at least one alkene functionality. The term "alkynyl" refers to a straight-chained or branched carbon-containing chain including at least one alkyne functionality. The term "aryl" refers to a carbon-containing ring bearing a system of conjugated double bonds often comprising at least six it (pi) electrons. Examples of aryl groups include, but are not limited to, phenyl, naphthyl, anysyl, toluoyl, xylenyl, and the like. The term "aralkyl" refers to an alkyl group substituted with at least one aryl group. The term "aralkenyl" refers to an alkenyl group substituted with at least one aryl group.

A radical is "straight-chained" when it has less than 0.1 mole percent of side chains having 1 or more carbon atoms. In some embodiments, a radical is straight-chained if it has less than 0.01 mole percent of such side chains. In some embodiments, a radical is straight-chained if it has less than 0.001 mole percent of such side chains. A radical is "branched" when it has more than 0.1 mole percent of side chains having 1 or more carbon atoms. In some embodiments, a radical is branched when it has more than 0.01 mole percent of such side chains. In some embodiments, a radical is branched when it has more than 0.001 mole percent of such side chains.

The terms "radical," "group," "functional group," and "substituent" can be used interchangeably in some contexts and can be used together to further describe a chemical structure. For example, the term "functional group" can refer to a chemical "group" or "radical," which is a chemical structure variable that can be in-chain, pendant and/or terminal to the chemical structure. A functional group may be substituted. Examples of substituents in substituted radicals include, but are not limited to, hydroxyls, alkyls, carboxyls, esters, aminos, amidos, iminos and combinations thereof. Such a functional group can also, for example, contain a heteroatom. Examples of heteroatoms of the hetero-radicals include, but are not limited to, sulfur, phosphorous, oxygen, nitrogen and combinations thereof.

In some embodiments, the functional groups can include, but are not limited to, oxygen-containing groups such as, for example, alcohols, ethers, phenols, and derivatives thereof. Such oxygen-containing groups include, but are not limited to, acetonides, alcohols, alkoxides, bisphenols, carbinols, cresols, diols, enols, enolates, epoxides, ethers, glycols, hydroperoxides, peroxides, phenols, phenolates, phenoxides, pinacols, trioxides, and ynols.

In some embodiments, the functional groups can include, but are not limited to, oxygen-containing groups such as, for example, aldehydes, ketones, quinones and derivatives thereof. Such oxygen-containing groups include, but are not limited to, acetals, acyloins, aldehydes, carbonyl compounds, diosphenols, dypnones, hemiacetals, hemiketals, ketals, ketenes, keto compounds, ketones, quinhydrones, quinomethanes, quinines, and combinations thereof.

In some embodiments, the functional groups can be oxygen-containing groups including, but not limited to, carboxylic acids, oxoacids, sulfonic acids, acid anhydrides, acid thioanhydrides, acyl groups, acyl halides, acylals, anhydrides, carboxylic acids, cyclic acid anhydrides, cyclic anhydrides, esters, fulgides, lactides, lactols, lactones, macrolides, naphthenic acids, ortho acids, ortho esters, oxo carboxylic acids, peroxy acids, and combinations thereof.

In some embodiments, the functional groups can include, but are not limited to, nitrogen-containing groups containing one nitrogen such as, for example, aldimines, aldoximes, alkoxyamines, amic acids, amides, amines, amine oxides, amine ylides, carbamates, hemiaminals, carbonitriles, carboxamides, isocyanides, cyanates, isocyanates, diisocyanates, cyanides, cyanohydrins, diacylamines, enamines, fulminates, hemiaminals, hydroxamic acids, hydroximic acids, hydroxylamines, imides, imidic acids, imidines, imines, oximes, isoureas, ketenimines, ketimines, ketoximes, lactams, lactims, nitriles, nitro, nitroso, nitrosolic acids, oxime O-ethers, quaternary ammonium compounds, quinone imines, quinonoximes, azomethines, ureides, urethanes, and combinations thereof.

In some embodiments, the functional groups can include, but are not limited to, nitrogen-containing groups containing two or more nitrogens such as, for example, aldazines, amide hydrazones, amide oximes, amidines, amidrazones, aminals, amine imides, amine imines, isodiazenes, azans, azides, azo imides, azines, azo compounds, azomethine imides, azoxy compounds, carbodiimides, carboxamidines, diamidides, diazo compounds, diazoamino compounds, diazoates, diazooxides, formamidine disulfides, formazans, hydrazides, hydrazide hydrazones, hydrazide imides, hydrazidines, hydrazines, hydrazo compounds, hydrazones, ketazines, nitramines, nitrile imines, nitrimines, nitrolic acids, nitrosamides, nitrosamines, nitrosimines, ortho amides, semicarbazones, semioxamazones, triazanes, triazenes, and combinations thereof.

In some embodiments, the functional groups can include, but are not limited to, sulfur-containing groups such as sulfones, sulfides, sulfinamides, sulfilimines, sulfimides, sulfinamides, sulfinamidines, sulfines, sulfinic acids, sulfinic anhydrides, sulfinylamines, sulfonamides, sulfones, sulfonediimines, sulfonic acids, sulfonic anhydrides, sulfoxides, sulfoximides, sulphur diimides, thio, thioacetals, thioaldehydes, thioanhydrides, thiocarboxylic acids, thiocyanates, thioether, thiohemiacetals, thioketones, thiol, thiolates, xanthic acids, and combinations thereof.

In some embodiments, the functional groups can include, but are not limited to, silyl groups, halogens, selenoethers, trifluoromethyls, thio-derivatives of urethanes where at least one oxygen atom is replaced by a sulfur atom, phosphoryls, phosphonates, phosphinates, and combinations thereof. In some embodiments, the functional groups are capable of free-radical polymerization and can include, but are not limited to, ethylenically unsaturated groups such as, for example, allyl, vinyl, acryloyl and methacrylol, and maleate and maleimido; and combinations thereof. In some embodiments, the functional groups include halides. In some embodiments, the functional group may include light scattering groups, magnetic groups, nanogold, other proteins, a solid matrix, radiolabels, carbohydrates, and combinations thereof.

The coating may at least substantially promote development of the functional endothelium as the source of the thrombomodulin when compared to a control development of such endothelium formation observed following CBD or TCHation of a metal or polymer drug-eluting medical device. In some embodiments, the medical device comprises an CBD or TCH.

One of skill will appreciate that a functional endothelium exists, or is promoted, for example, where the amount of thrombomodulin in the functional endothelium is in a quantity sufficient to show a statistical difference in an amount of thrombus formation when compared to a control development of such an endothelium, or lack thereof, observed following CBD or TCHation of a control metal or polymer drug-eluting device. In some embodiments, the functional endothelium has been promoted where it can produce an amount of thrombomodulin that is substantially greater than an amount of thrombomodulin observed from a control medical device. An amount of thrombomodulin is "substantially greater" when the desired anti-thrombus effect is statistically improved over that observed from a control medical device. In some embodiments, a functional endothelium exists, or has been promoted, where the desired effects of thrombus inhibition, restenosis inhibition, and/or blood flow improvement from the presence of thrombomodulin becomes statistically observable when compared to a control development of such endothelium formation observed following CBD or TCHation of a metal or polymer drug-eluting medical device that does not delay the onset of drug-elution for at least 5, 10, 12, 14, 15, 20, 25, 30, 45, 60, 75, or 90 days, or any range therein.

In addition, the coating may at least substantially inhibit development of a hyperproliferative tissue when compared to a control development of such hyperproliferative tissue observed following CBD or TCHation of a metal or polymer medical device that does not elute a drug. One of skill will appreciate, for example, that hyperproliferative tissue growth includes a growth of tissue beyond what is normal and healthy. It can cause adverse effects on the function or physiology of the subject.

The inhibition of the development of a hyperproliferative tissue can occur, or be promoted, when the amount of such tissue is in a quantity sufficient to show a statistical difference in an amount of tissue formation when compared to a control development of such an tissue, or lack thereof, observed following CBD or TCHation of a control metal or polymer medical device that does not elute a drug. In some embodiments, the amount of hyperproliferative tissue produced from the control device is substantially greater than an amount of tissue observed from a medical device having a coating taught herein. An amount of tissue can be considered "substantially greater" when the measured amount is statistically greater. In some embodiments, restenosis is inhibited by at least 5, 10, 12, 14, 15, 20, 25, 30, 45, 60, 75, 90, 95, 99, 100 percent, or any amount therein, when compared to a control development of such restenosis formation observed following CBD or TCHation of a metal or polymer medical device that does not elute a drug.

The coatings can be designed for a predetermined delay time and release rate of the drug. As described above, layers and sub-layers of coatings can be designed to have a different composition to impart more control over drug elution, coating hydrolysis, coating strength and integrity, other physical traits, and other such coating characteristics known to one of skill. In some embodiments, for example, the drug-reservoir layer can further comprise an accelerant layer to accelerate the time to onset of drug elution. In fact, in some embodiments, the accelerant layer can have a poly(lactic-co-glycolic acid) with acid terminal groups, a monomer ratio of lactic acid to glycolic acid that ranges from about 85:15 to about 50:50, and a molecular weight that ranges from about 90 KDaltons to about 120 KDaltons.

And, as described above, other variables, such as layer or sub-layer thickness, and/or thickness ratios between layers and/or sub-layers, can be used to obtain a desired delay time for drug release, release rate of the drug, fluid uptake in the coating, as well as coating strength, integrity, and the like. In some embodiments, the thickness of the coating can range from about 2 microns to about 9 microns, from about 1 micron to about 40 microns, from about 1 micron to about 30 microns, from about 2 microns to about 38 microns, from about 3 microns to about 36 microns, from about 4 microns to about 34 microns, from about 5 microns to about 7 microns, from about 4 microns to about 6 microns, or any range therein. In some embodiments, the thickness of the coating is less than 12 microns, less than 11 microns, less than 9 microns, less than 8 microns, less than 7 microns, less than 6 microns, less than 5 microns, or any range therein, such as, for example, from 7 microns to 12 microns, 9 microns to 12 microns, or 7 microns to 9 microns. In some embodiments, each layer or sub-layer can range from about 0.1 micron to about 10 microns, from about 0.1 micron to about 7 microns, from about 0.1 micron to about 5 microns, from about 0.1 micron to 3 microns, from about 0.1 micron to about 2 microns, from about 0.1 micron to about 0.9 microns, from about 0.1 micron to about 0.8 microns, from about 0.1 micron to about 0.7 microns, from about 0.1 micron to about 0.6 microns, from about 0.1 micron to about 0.5 microns, from about 0.1 micron to about 0.4 microns, from about 0.1 micron to about 0.3 microns, from about 0.3 micron to about 0.8 microns, from about 0.2 microns to about 5 microns, from about 0.2 microns to about 4 microns, from about 0.3 microns to about 3 microns, from about 0.5 microns to about 5 microns, from about 0.6 microns to about 3 microns from about 1 micron to about 3 microns, or any range therein.

In some embodiments, for example, the thickness ratio of the drug-reservoir layer to the drug-containing layer can range from about 4:1 to about 10:1, from about 4:1 to about 7:1, from about 2:1 to about 12:1, from about 3:1 to about 11:1, from about 5:1 to about 10:1, from about 2:1 to about 8:1, from about 4:1 to about 6:1, or any range therein. In some embodiments, the ratio can be a mass ratio, where the mass of the drug-reservoir layer to the mass of the drug-containing layer can range from 3:1 to 20:1, from 4:1 to 16:1, from 5:1 to 15:1, from 6:1 to 10:1, or any range therein.

In some embodiments thinner coatings and desired ratios can be achieved using higher percentages of drug in the drug-containing layer, where in some embodiments, the drug-containing layer is composed of 100, 99, 98, 97, 96, 95, 94, 93, 92, 91, 90 percent drug, or any range therein. The drug-containing layer can range from about 0.05 to about 5 microns, from about 0.03 to about 3 microns, from about 0.1 to about 2 microns, or any range therein in thickness, in some embodiments.

The relative hydrophobicity or hydrophilicity can also impart desired drug retention and elution behavior from the coating. For example, the miscibility of the drug in a coating can be preselected to affect the rate of drug migration in the coating, and/or elution from the coating. In some embodiments, the drug can be selected to be miscible in a coating to increase retention time in the coating. Likewise, in some embodiments, the drug can be selected to be less miscible, or immiscible, in a coating to decrease retention time in the coating.

As such, the teachings are generally directed to a method of inhibiting the formation of hyperproliferative tissue and promoting the formation of a functional endothelium after CBD or TCHation of a medical device in a subject. The method can comprise applying a therapeutic coating on a medical device and CBD or TCHing the device in the subject. In some embodiments, the coating can comprise a biodegradable drug-containing layer that (i) is positioned over a surface of a medical device and (ii) serves as a source of a drug that functions as an anti-proliferative agent in a subject; and, a biodegradable drug-reservoir layer positioned over a surface of the drug-containing layer and comprising a drug-retaining layer, the drug-retaining layer remaining void or substantially void of the drug at a time of CBD or TCHation in the subject and functioning to retain and at least substantially block an initial release of the drug into the subject for a time sufficient to form a functional endothelium over the surface of the medical device, the functional endothelium providing a source of thrombomodulin to the subject.

One of skill will appreciate that a coating can be applied using any one, or any combination, of methods known in the art, where the terms "form" and "apply" can be used interchangeably, in some embodiments. The compositions can be in the form of coatings for medical devices such as, for example, a balloon-expandable breast CBD or TCH. There are many coating configurations possible, and each configuration can include any number and combination of layers. In some embodiments, the coatings can comprise one or a combination of the following four types of layers: (a) an agent layer, which may comprise a polymer and an agent or, alternatively, a polymer free agent; (b) an optional primer layer, which may improve adhesion of subsequent layers on the CBD or TCHable substrate or on a previously formed layer; (c) an optional topcoat layer, which may serve as a way of controlling the rate of release of an agent; and (d) an optional biocompatible finishing layer, which may improve the biocompatibility of the coating.

In some embodiments, any one or any combination of layers can be used. And, each layer can be applied to an CBD or TCHable substrate, for example, by any method including, but not limited to, dipping, spraying, pouring, brushing, spin-coating, roller coating, meniscus coating, powder coating, inkjet-type application or a combination thereof. In one example, each of the layers can be formed on an CBD or TCH by dissolving one or more biodegradable polymers, optionally with a non-biodegradable polymer, in one or more solvents and either (i) spraying the solution on the CBD or TCH or (ii) dipping the CBD or TCH in the solution. In this example, a dry coating of biodegradable polymer may be formed on the CBD or TCH when the solvent evaporates.

The formation of each layer may involve use of a casting solvent. A casting solvent is a liquid medium within which a polymer can be solubilized to form a solution that may be applied as a coating on a substrate. The casting solvent must be selected to avoid adversely affecting an underlying material such as, for example, an underlying primer layer or a bare CBD or TCH structure. In one example, a material used to form the primer layer is soluble in a highly polar casting solvent but is reasonably insoluble in a low polarity casting solvent. A material is "reasonably insoluble" in a solvent when the material does not solubilize to an extent great enough to significantly affect the performance of the resulting product, meaning that the product can still be used for its intended purpose. In this example, an overlying agent layer that is soluble in a low polarity casting solvent can be applied to the underlying primer layer without disrupting the structure of primer layer.

The casting solvent may be chosen based on several criteria including, for example, its polarity, ability to hydrogen bond, molecular size, volatility, biocompatibility, reactivity and purity. Other physical characteristics of the casting solvent may also be taken into account including the solubility limit of the polymer in the casting solvent, the presence of oxygen and other gases in the casting solvent, the viscosity and vapor pressure of the combined casting solvent and polymer, the ability of the casting solvent to diffuse through an underlying material, and the thermal stability of the casting solvent.

One of skill in the art has access to scientific literature and data regarding the solubility of a wide variety of polymers. Furthermore, one of skill in the art will appreciate that the choice of casting solvent may begin empirically by calculating the Gibb's free energy of dissolution using available thermodynamic data. Such calculations allow for a preliminary selection of potential solvents to test in a laboratory. It is recognized that process conditions can affect the chemical structure of the underlying materials and, thus, affect their solubility in a casting solvent. It is also recognized that the kinetics of dissolution are a factor to consider when selecting a casting solvent, because a slow dissolution of an underlying material, for example, may not affect the performance characteristics of a product where the product is produced relatively quickly.

Casting solvents for use in the present invention include, but are not limited to, DMAC, DMF, THF, cyclohexanone, xylene, toluene, acetone, i-propanol, methyl ethyl ketone, propylene glycol monomethyl ether, methyl butyl ketone, ethyl acetate, n-butyl acetate, and dioxane. Solvent mixtures can be used as well. Examples of the mixtures include, but are not limited to, DMAC and methanol (50:50 w/w); water, i-propanol, and DMAC (10:3:87 w/w); i-propanol and DMAC (80:20, 50:50, or 20:80 w/w); acetone and cyclohexanone (80:20, 50:50, or 20:80 w/w); acetone and xylene (50:50 w/w); acetone, xylene and FLUX REMOVER AMS (93.7% 3,3-dichloro-1,1,1,2,2-pentafluoropropane and 1,3-dichloro-1,1,2,2,3-pentafluoropropane, and the balance is methanol with trace amounts of nitromethane; Tech Spray, InC) (10:40:50 w/w); and 1,1,2-trichloroethane and chloroform (80:20 w/w).

It should be appreciated that a process of forming a medical article or coating can include additional process steps such as, for example, the use of energy such as heat, electromagnetic radiation, electron beam, ion or charged particle beam, neutral-atom beam, and chemical energy. The process of drying can be accelerated by using higher temperatures.

A medical article or coating can also be annealed to enhance the mechanical properties of the composition Annealing can be used to help reduce part stress and can provide an extra measure of safety in applications such as complex medical devices, where stress-cracking failures can be critical. The annealing can occur at a temperature that ranges from about 30 degrees C. to about 200 degrees C., from about 35 degrees C. to about 190 degrees C., from about 40 degrees C. to about 180 degrees C., from about 45 degrees C. to about 175 degrees C., or any range therein. The annealing time can range from about 1 second to about 60 seconds, from about 1 minute to about 60 minutes, from about 2 minute to about 45 minutes, from about 3 minute to about 30 minutes, from about 5 minute to about 20 minutes, or any range therein. The annealing can also occur by cycling heating with cooling, wherein the total time taken for heating and cooling is the annealing cycle time.

In some embodiments, the drug-containing layer can be applied as a solvent mixture and the solvent can be dried after application using a substantially non-reactive heated gas. The drying can serve to at least substantially inhibit mobilization of the drug from the drug-containing layer during application of additional layers in the formation of the coating. The amount of mobilization of the drug can be considered "substantially inhibited" when the measured amount of mobilization of the drug from the drug-containing layer is statistically less than if the drying procedure was not used as taught herein.

The application of the sub-layers can be used to at least substantially promote a retention of the drug in the drug-containing layer during formation of the coating when compared to such a coating without the application of the sub-layers. The amount of retention of the drug can be considered "substantially promoted" when the measured amount of retention of the drug from the drug-containing layer is statistically greater than if the sub-layer application as taught herein was not used.

In some embodiments, the drug-retaining layer can comprise at least one sub-layer having a thickness of less than or equal to 3 microns, where a repeated application of the sub-layer can be used to form thicknesses of greater than 3 microns. In some embodiments, the accelerant layer can be positioned between the drug-containing layer and the remainder of the drug-retaining layer, is more hydrophilic than the remainder of the drug-retaining layer, and comprises at least one sub-layer having a thickness of less than or equal to 3 microns, where a repeated application the sub-layer is used to form thicknesses of greater than 3 microns. The accelerant layer can contain some of the drug. In some embodiments, the drug composes less than 30, 25, 20, 15, 10, 7, 5, 4, 3, 2, 1 percent, or any amount therein, of the accelerant layer. And, in some embodiments the drug composes less than 10 percent of the accelerant layer.

The coatings can be heterogeneous in morphology. For example, a hydrophobic layer can contain hydrophilic regions. Likewise, a more hydrophilic coating can have hydrophobic regions. The hydrophilic regions can be in the form of isolated packages of material, or "islands" in some embodiments, where the isolated hydrophilic package can add to the water absorption rate, and thus hydrolysis rate, of the coating. The isolated packages may be added during the coating process as droplets, in some embodiments. The coatings taught herein can, in some embodiments, further comprise pockets of hydrophilic material in the drug-retaining layer, wherein the hydrophilic material can comprise a second drug. There can be one or more such pockets, and the pockets can be positioned anywhere throughout the coating. In some embodiments, one or more hydrophilic pockets are positioned in the drug reservoir layer and, in some embodiments, one or more hydrophilic pockets are positioned in the drug-retaining layer. In some embodiments, the hydrophilic pockets comprise a drug selected from the group consisting of dextran, heparin, ticlopidine, chlopidogrel, enoxaparin, dalteparin, hirudin, bivalirudin, argatroban, and danparoid.

The coating can be applied to a surface of a medical device using, for example, wet chemistry and acetone as a solvent with techniques known to one of skill. At least one drug and polymer is dissolved into the volatile solvent to form a drug solution, and the drug can be an anti-proliferative, such as rapamycin. The volatile solvent can be acetone, dichloromethane, or a mixture of the two solvents.

In one example, about 1-2 micron of a drug-containing layer can be covered with a 1-3 micron accelerant layer made of acid terminated 75/25 monomer ratio PLGA having a molecular weight of 90-120 KDalton, and the accelerant layer can be covered with about 6-12 microns of ester terminated 75/25 monomer ratio PLGA having a molecular weight of 100-160 KDalton. This unique and novel combination of compositions in different layers, as well as the relative thicknesses and positioning of the layers, can provide a coating having a desired delay in the onset of drug elution. The elution, in fact, can be delayed for a designed, prolonged period of time, at which time the drug release is fast enough to have a therapeutic effect. The coating is robust, maintaining functional integrity through stresses and strains of assembly and deployment. And, the coating can maintain a low enough profile of the CBD or TCH for ease of delivery and introducing less foreign material into the body.

The following is an example of a process that can be used to create composite elution layers, a process comprising multiple sub-layer applications, such as those described herein. The drug is added to the solvent for wet chemistry application, and the drug-containing layer may be applied to the surface of the device. The drug-containing layer can be 120 nanometers and 6 microns, 200 nanometers and 3 microns, 0.7-1.1 microns, or any range therein, thick in some embodiments. The drug-containing layer is then dried with convection of a non-reactive gas, such as nitrogen, at a temperature elevated above room temperature.

The accelerant layer polymer is mixed with a solvent for wet chemistry application, and the accelerant layer is created by layering multiple sub-layers of the same material. Each sub-layer is coated onto previous layer and dried with convection of gas as described in above using a drying time of about 1-2 hours before coating the next sub-layer/layer. The accelerant layer can be about 1-2 microns thick and composed of 50:50 PLGA with acid terminal end-groups. In some embodiments, the accelerant layer can be about 3-5 microns thick and composed of 2-3 sub-layers of 75:25 PLGA with acid terminal end-groups. And, in some embodiments, the accelerant layer can be between about 120 nanometers and 6 microns, 400 nanometers and 4 microns, 500 nanometers and 5 microns, or any range therein. Moreover, the concentration of the drug in the accelerant layer can be less than 50% of the drug-containing layer before CBD or TCHation in some embodiments.

The drug-retaining layer can then be prepared and coated onto the accelerant layer and dried. The drug-retaining layer is applied by layering multiple sub-layers of the same material. Each sub-layer is coated onto previous layer and dried using convection of gas as described above with drying times of about 1-2 hours before coating the next sub-layer/layer. The drug-retaining layer can be about 3-5 times the thickness of the accelerant layer, in some embodiments, if the accelerant layer is composed of 50:50 PLGA having an ester terminal end-group in some embodiments. In some embodiments, the thickness of the drug-retaining layer can be about 0.2-2 times that of the accelerant layer, if the accelerant layer is composed of 75:25 PLGA having an ester terminal end-group. The entire assembly may then be packaged and sterilized for deployment.

One of skill will appreciate that any non-reactive or substantially non-reactive gas can be used including, but not limited to, nitrogen, carbon dioxide, or a noble gas. The heated gas's temperature can be, for example, between about 70 degrees F. and the drug's melting point. In some embodiments, the gas's temperature can be between about 70 degrees F. and 240 degrees F., from 140-190 degrees F., or any range therein. The specified drying time can be, for example, between about 0 minutes and 3 hours, 10-30 minutes, 30 minutes and 1 hour, 15 minutes and 2 hours, or any range therein. The gas surface flow rate can be between about 40 and 500 inches per second, 50 and 400 inches per second, 100 and 500 inches per second, or any range therein. In some embodiments, the gas surface flow rate is 90-150 inches/sec It should be appreciated that, in some embodiments, the term "agent" or "drug" can be used interchangeably. An "agent" or "drug" can be a moiety, for example, that may be bioactive, biobeneficial, diagnostic, plasticizing, or have a combination of these characteristics. A "moiety" can be a functional group composed of at least 1 atom, a bonded residue in a macromolecule, an individual unit in a copolymer or an entire polymeric block. It is to be appreciated that any medical articles that can be improved through the teachings described herein are within the scope the invention.

A "bioactive agent" is a moiety that can be combined with a polymer and provides a therapeutic effect, a prophylactic effect, both a therapeutic and a prophylactic effect, or other biologically active effect within a subject. Moreover, the bioactive agents of the present invention may remain linked to a portion of the polymer or be released from the polymer. A "biobeneficial agent" is an agent that can be combined with a polymer and provide a biological benefit within a subject without necessarily being released from the polymer.

In one example, a biological benefit may be that the polymer or coating becomes non-thrombogenic, such that protein absorption is inhibited or prevented to avoid formation of a thromboembolism; promotes healing, such that endothelialization within a blood vessel is not exuberant but rather forms a healthy and functional endothelial layer; or is non-inflammatory, such that the biobeneficial agent acts as a biomimic to passively avoid attracting monocytes and neutrophils, which could lead to an event or cascade of events that create inflammation.

A "diagnostic agent" is a type of bioactive agent that can be used, for example, in diagnosing the presence, nature, or extent of a disease or medical condition in a subject. In one embodiment, a diagnostic agent can be any agent that may be used in connection with methods for imaging an internal region of a patient and/or diagnosing the presence or absence of a disease in a patient. Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, and radiofrequency (RF) and microwave lasers. Diagnostic agents may also include any other agents useful in facilitating diagnosis of a disease or other condition in a patient, whether or not imaging methodology is employed.

Examples of biobeneficial agents include, but are not limited to, many of the polymers listed above such as, for example, carboxymethylcellulose; poly(alkylene glycols) such as, for example, PEG; poly(N-vinyl pyrrolidone); poly(acrylamide methyl propane sulfonic acid); poly(styrene sulfonate); sulfonated polysaccharides such as, for example, sulfonated dextran; sulfated polysaccharides such as, for example, sulfated dextran and dermatan sulfate; and glycosaminoglycans such as, for example, hyaluronic acid and heparin; and any derivatives, analogs, homologues, congeners, salts, copolymers and combinations thereof. In some embodiments, the biobeneficial agents can be prohealing such as, for example, poly(ester amides), elastin, silk-elastin, collagen, atrial natriuretic peptide (ANP); and peptide sequences such as, for example, those comprising Arg-Gly-Asp (RGD). In other embodiments, the biobeneficial agents can be non-thrombotics such as, for example, thrombomodulin; and antimicrobials such as, for example, the organosilanes. It is to be appreciated that one skilled in the art should recognize that some of the groups, subgroups, and individual biobeneficial agents may not be used in some embodiments of the present invention.

Examples of heparin derivatives include, but are not limited to, earth metal salts of heparin such as, for example, sodium heparin, potassium heparin, lithium heparin, calcium heparin, magnesium heparin, and low molecular weight heparin. Other examples of heparin derivatives include, but are not limited to, heparin sulfate, heparinoids, heparin-based compounds and heparin derivatized with hydrophobic materials.

Examples of hyaluronic acid derivates include, but are not limited to, sulfated hyaluronic acid such as, for example, O-sulphated or N-sulphated derivatives; esters of hyaluronic acid wherein the esters can be aliphatic, aromatic, arylaliphatic, cycloaliphatic, heterocyclic or a combination thereof; crosslinked esters of hyaluronic acid wherein the crosslinks can be formed with hydroxyl groups of a polysaccharide chain; crosslinked esters of hyaluronic acid wherein the crosslinks can be formed with polyalcohols that are aliphatic, aromatic, arylaliphatic, cycloaliphatic, heterocyclic, or a combination thereof; hemiesters of succinic acid or heavy metal salts thereof; quaternary ammonium salts of hyaluronic acid or derivatives such as, for example, the O-sulphated or N-sulphated derivatives.

Examples of poly(alkylene glycols) include, but are not limited to, PEG, mPEG, poly(ethylene oxide), poly(propylene glycol)(PPG), poly(tetramethylene glycol), and any derivatives, analogs, homologues, congeners, salts, copolymers and combinations thereof. In some embodiments, the poly(alkylene glycol) is PEG. In other embodiments, the poly(alkylene glycol) is mPEG. In other embodiments, the poly(alkylene glycol) is poly(ethylene glycol-co-hydroxybutyrate).

The copolymers that may be used as biobeneficial agents include, but are not limited to, any derivatives, analogs, homologues, congeners, salts, copolymers and combinations of the foregoing examples of agents. Examples of copolymers that may be used as biobeneficial agents in the teachings herein include, but are not limited to, dermatan sulfate, which is a copolymer of D-glucuronic acid or L-iduronic acid and N-acetyl-D-galactosamine; poly(ethylene oxide-co-propylene oxide); copolymers of PEG and hyaluronic acid; copolymers of PEG and heparin; copolymers of PEG and hirudin; graft copolymers of poly(L-lysine) and PEG; copolymers of PEG and a poly(hydroxyalkanoate) such as, for example, poly(ethylene glycol-co-hydroxybutyrate); and any derivatives, analogs, congeners, salts, or combinations thereof. In some embodiments, the copolymer that may be used as a biobeneficial agent can be a copolymer of PEG and hyaluronic acid, a copolymer of PEG and hirudin, and any derivative, analog, congener, salt, copolymer or combination thereof. In other embodiments, the copolymer that may be used as a biobeneficial agent is a copolymer of PEG and a poly(hydroxyalkanoate) such as, for example, poly(hydroxybutyrate); and any derivative, analog, congener, salt, copolymer or combination thereof.

The bioactive agents can be any moiety capable of contributing to a therapeutic effect, a prophylactic effect, both a therapeutic and prophylactic effect, or other biologically active effect in a mammal. The agent can also have diagnostic properties. The bioactive agents include, but are not limited to, small molecules, nucleotides, oligonucleotides, polynucleotides, amino acids, oligopeptides, polypeptides, and proteins. In one example, the bioactive agent inhibits the activity of vascular smooth muscle cells. In another example, the bioactive agent controls migration or proliferation of smooth muscle cells to inhibit restenosis.

Bioactive agents include, but are not limited to, antiproliferatives, antineoplastics, antimitotics, anti-inflammatories, antiplatelets, anticoagulants, antifibrins, antithrombins, antibiotics, antiallergics, antioxidants, and any prodrugs, metabolites, analogs, homologues, congeners, derivatives, salts and combinations thereof. It is to be appreciated that one skilled in the art should recognize that some of the groups, subgroups, and individual bioactive agents may not be used in some embodiments of the present invention.

Antiproliferatives include, for example, actinomycin D, actinomycin IV, actinomycin I1, actinomycin X1, actinomycin C1, and dactinomycin (COSMEGEN, Merck & Co., InC). Antineoplastics or antimitotics include, for example, paclitaxel (TAXOL, Bristol-Myers Squibb Co.), docetaxel (TAXOTERE, Aventis S.A.), methotrexate, azathioprine, vincristine, vinblastine, fluorouracil, doxorubicin hydrochloride (ADRIAMYCIN, Pfizer, InC) and mitomycin (MUTAMYCIN, Bristol-Myers Squibb Co.), and any prodrugs, metabolites, analogs, homologues, congeners, derivatives, salts and combinations thereof.

Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethyl ketone (synthetic antithrombin), dipyridamole, glycoprotein IIb/IIIa platelet membrane receptor antagonist antibody, recombinant hirudin, and thrombin inhibitors (ANGIOMAX, Biogen, InC), and any prodrugs, metabolites, analogs, homologues, congeners, derivatives, salts and combinations thereof.

Cytostatic or antiproliferative agents include, for example, angiopeptin, angiotensin converting enzyme inhibitors such as captopril (CAPOTEN and CAPOZIDE, Bristol-Myers Squibb Co.), cilazapril or lisinopril (PRINIVIL and PRINZIDE, Merck & Co., InC); calcium channel blockers such as nifedipine; colchicines; fibroblast growth factor (FGF) antagonists; fish oil (omega 3-fatty acid); histamine antagonists; lovastatin (MEVACOR, Merck & Co., InC); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof. Antiallergic agents include, but are not limited to, pemirolast potassium (ALAMAST, Santen, InC), and any prodrugs, metabolites, analogs, homologues, congeners, derivatives, salts and combinations thereof.

Other bioactive agents useful in the teachings herein include, but are not limited to, free radical scavengers; nitric oxide donors; rapamycin; methyl rapamycin; 42-Epi-(tetrazoylyl) rapamycin (ABT-578); everolimus; tacrolimus; 40-O-(2-hydroxy)ethyl-rapamycin; 40-O-(3-hydroxy)propyl-rapamycin; 40-O-[2-(2-hydroxy)ethoxy]ethyl-rapamycin; tetrazole containing rapamycin analogs; estradiol; clobetasol; idoxifen; tazarotene; alpha-interferon; host cells such as epithelial cells; genetically engineered epithelial cells; dexamethasone; and any prodrugs, metabolites, analogs, homologues, congeners, derivatives, salts and combinations thereof.

Free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (4-hydroxy-TEMPO), 2,2',3,4,5,5'-hexamethyl-3-imidazolinium-1-yloxy methyl sulfate, free radical; 4-carboxy-2,2',6,6'-tetramethyl-1-piperinyloxy, free radical (4-carboxy-TEMPO); 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate and any analogs, homologues, congeners, derivatives, salts and combinations thereof. The drugs eluted from the coatings taught herein can function as an anti-proliferative or immunosuppressant. In some embodiments, the drug can be rapamycin or a derivative of rapamycin. And, in some embodiments, the drug can be selected from the group consisting of fluoroquinolone, paclitaxel, rapamycin, sirolimus, everolimus, biolimus, zotarolimus, tacrolimus, fibroblast growth factor (bFGF), rapamycin analogs, antisense dexamethasone, angiopeptin, BATIMISTAT, tranilast, transilast, halofuginon, acetylsalicylic acid, hirudin, steroids, ibuprofen, antimicrobials, antibiotics, actinomycin D, tissue plasma activators, and estradiol. One of skill will appreciate that agents that affect vascular smooth muscle cell (VSMC) proliferation or migration can also be used in some embodiments, including, but not limited to transcription factor E2F1.

The agents of the present invention can be used alone or in combination with other agents to obtain other desired functions of the polymeric compositions. The amounts of the agents that compose the polymeric compositions vary according to a variety of factors including, but not limited to, the biological activity of the agent; the age, body weight, response, or the past medical history of the subject; the type of atherosclerotic disease; the presence of systemic diseases such as, for example, diabetes; the pharmacokinetic and pharmacodynamic effects of the agents or combination of agents; and the design of the compositions for sustained release of the agents. Factors such as these are routinely considered by one of skill in the art when administering an agent to a subject in a desired amount to obtain a desired effect. In some embodiments, the desired amount is termed an "effective amount," where the amount administered elicits a desired response. In some embodiments, the effective amount can be a "therapeutically effective amount", administered in an amount that prevents, inhibits, or ameliorates the symptoms of a disease.

It is to be appreciated that the design of a composition for drug release can be dependent on a variety of factors such as, for example, the therapeutic, prophylactic, ameliorative or diagnostic needs of a patient or condition. In some embodiments, the agent can comprise an antiproliferative and should have a sustained release ranging from about 1 week to about 10 weeks, from about 2 weeks to about 8 weeks, from about 3 weeks to about 7 weeks, from about 4 weeks to about 6 weeks, and any range therein. In some embodiments, the agent can comprise an anti-inflammatory and should have a sustained release ranging from about 6 hours to about 3 weeks, from about 12 hours to about 2 weeks, from about 18 hours to about 10 days, from about 1 day to about 7 days, from about 2 days to about 6 days, or any range therein. In general, the sustained release should range from about 4 hours to about 12 weeks; alternatively, from about 6 hours to about 10 weeks; or from about 1 day to about 8 weeks.

Effective amounts, for example, may be extrapolated from in vitro or animal model systems. In some embodiments, the agent or combination of agents have a concentration that ranges from about 0.001% to about 75%; from about 0.01% to about 70%; from about 0.1% to about 60%; from about 0.25% to about 60%; from about 0.5% to about 50%; from about 0.75% to about 40%; from about 1.0% to about 30%; from about 2% to about 20%; and any range therein, where the percentage is based on the total weight of the polymer and agent or combination of agents.

The medical devices discussed herein can be any devices known to one of skill to benefit from the teachings provided. A medical device, for example, can be comprised of a metal or an alloy, including, but not limited to, ELASTINITE, NITINOL, stainless steel, tantalum, tantalum-based alloys, nickel-titanium alloy, platinum, platinum-based alloys such as, for example, platinum-iridium alloys, iridium, gold, magnesium, titanium, titanium-based alloys, zirconium-based alloys, alloys comprising cobalt and chromium (EL-GILOY, Elgiloy Specialty Metals, InC; MP35N and MP20N, SPS Technologies) or combinations thereof. The tradenames "MP35N" and "MP20N" describe alloys of cobalt, nickel, chromium and molybdenum. The MP35N consists of 35% cobalt, 35% nickel, 20% chromium, and 10% molybdenum. The MP20N consists of 50% cobalt, 20% nickel, 20% chromium, and 10% molybdenum. Medical devices with structural components that, are comprised of bioabsorbable polymers or biostable polymers are also included within the scope of the present invention.

The terms "plasticizer" and "plasticizing agent" can be used interchangeably in the teachings herein, and refer to any agent, including any agent described above, where the agent can be added to a polymeric composition to modify the mechanical properties of the composition or a product formed from the composition. Plasticizers can be added, for example, to reduce crystallinity, lower the glass-transition temperature (Tg), or reduce the intermolecular forces between polymers, with design goals that may include, but are not limited to, enhancing mobility between polymer chains in the composition. The mechanical properties that are modified include, but are not limited to, Young's modulus, impact resistance (toughness), tensile strength, and tear strength. Impact resistance, or "toughness," is a measure of energy absorbed during fracture of a polymer sample of standard dimensions and geometry when subjected to very rapid impact loading. Toughness can be measured using Charpy and Izod impact tests to assess the brittleness of a material.

A plasticizer can be monomeric, polymeric, co-polymeric, or a combination thereof, and can be combined with a polymeric composition in the same manner as described above for the biobeneficial and bioactive agents. Plasticization and solubility are analogous in the sense that selecting a plasticizer involves considerations similar to selecting a solvent such as, for example, polarity. Furthermore, plasticization can also be provided through covalent bonding by changing the molecular structure of the polymer through copolymerization.

Examples of plasticizing agents include, but are not limited to, low molecular weight polymers such as single-block polymers, multi-block polymers, and copolymers; oligomers such as ethyl-terminated oligomers of lactic acid; small organic molecules; hydrogen bond forming organic compounds with and without hydroxyl groups; polyols such as low molecular weight polyols having aliphatic hydroxyls; alkanols such as butanols, pentanols and hexanols; sugar alcohols and anhydrides of sugar alcohols; polyethers such as poly(alkylene glycols); esters such as citrates, phthalates, sebacates and adipates; polyesters; aliphatic acids; proteins such as animal proteins and vegetable proteins; oils such as, for example, the vegetable oils and animal oils; silicones; acetylated monoglycerides; amides; acetamides; sulfoxides; sulfones; pyrrolidones; oxa acids; diglycolic acids; and any analogs, derivatives, copolymers and combinations thereof.

In some embodiments, the plasticizers include, but are not limited to other polyols such as, for example, caprolactone diol, caprolactone triol, sorbitol, erythritol, glucidol, mannitol, sorbitol, sucrose, and trimethylol propane. In other embodiments, the plasticizers include, but are not limited to, glycols such as, for example, ethylene glycol, diethylene glycol, triethylene glycol, tetraethylene glycol, propylene glycol, butylene glycol, 1,2-butylene glycol, 2,3-butylene glycol, styrene glycol, pentamethylene glycol, hexamethylene glycol; glycol-ethers such as, for example, monopropylene glycol monoisopropyl ether, propylene glycol monoethyl ether, ethylene glycol monoethyl ether, and diethylene glycol monoethyl ether; and any analogs, derivatives, copolymers and combinations thereof.

In other embodiments, the plasticizers include, but are not limited to esters such as glycol esters such as, for example, diethylene glycol dibenzoate, dipropylene glycol dibenzoate, triethylene glycol caprate-caprylate; monostearates such as, for example, glycerol monostearate; citrate esters; organic acid esters; aromatic carboxylic esters; aliphatic dicarboxylic esters; fatty acid esters such as, for example, stearic, oleic, myristic, palmitic, and sebacic acid esters; triacetin; poly(esters) such as, for example, phthalate polyesters, adipate polyesters, glutate polyesters, phthalates such as, for example, dialkyl phthalates, dimethyl phthalate, diethyl phthalate, isopropyl phthalate, dibutyl phthalate, dihexyl phthalate, dioctyl phthalate, diisononyl phthalate, and diisodecyl phthalate; sebacates such as, for example, alkyl sebacates, dimethyl sebacate, dibutyl sebacate; hydroxyl-esters such as, for example, lactate, alkyl lactates, ethyl lactate, butyl lactate, allyl glycolate, ethyl glycolate, and glycerol monostearate; citrates such as, for example, alkyl acetyl citrates, triethyl acetyl citrate, tributyl acetyl citrate, trihexyl acetyl citrate, alkyl citrates, triethyl citrate, and tributyl citrate; esters of castor oil such as, for example, methyl ricinolate; aromatic carboxylic esters such as, for example, trimellitic esters, benzoic esters, and terephthalic esters; aliphatic dicarboxylic esters such as, for example, dialkyl adipates, alkyl allylether diester adipates, dibutoxyethoxyethyl adipate, diisobutyl adipate, sebacic esters, azelaic esters, citric esters, and tartaric esters; and fatty acid esters such as, for example, glycerol, mono- di- or triacetate, and sodium diethyl sulfosuccinate; and any analogs, derivatives, copolymers and combinations thereof.

In other embodiments, the plasticizers include, but are not limited to ethers and polyethers such as, for example, poly(alkylene glycols) such as poly(ethylene glycols) (PEG), polypropylene glycols), and poly(ethylene/propylene glycols); low molecular weight poly(ethylene glycols) such as, for example, PEG 400 and PEG 6000; PEG derivatives such as, for example, methoxy poly(ethylene glycol) (mPEG); and ester-ethers such as, for example, diethylene glycol dibenzoate, dipropylene glycol dibenzoate, and triethylene glycol caprate-caprylate; and any analogs, derivatives, copolymers and combinations thereof.

In other embodiments, the plasticizers include, but are not limited to, amides such as, for example, oleic amide, erucic amide, and palmitic amide; alkyl acetamides such as, for example, dimethyl acetamide and dimethyl formamide; sulfoxides such as for example, dimethyl sulfoxide; pyrrolidones such as, for example, n-methylpyrrolidone; sulfones such as, for example, tetramethylene sulfone; acids such as, for example, oxa monoacids, oxa diacids such as 3,6,9-trioxaundecanedioic acid, polyoxa diacids, ethyl ester of acetylated citric acid, butyl ester of acetylated citric acid, capryl ester of acetylated citric acid, and diglycolic acids such as dimethylol propionic acid; and any analogs, derivatives, copolymers and combinations thereof.

In other embodiments, the plasticizers can be vegetable oils including, but not limited to, epoxidized soybean oil; linseed oil; castor oil; coconut oil; fractionated coconut oil; epoxidized tallates; and esters of fatty acids such as stearic, oleic, myristic, palmitic, and sebacic acid. In other embodiments, the plasticizers can be essential oils including, but not limited to, angelica oil, anise oil, arnica oil, aurantii aetheroleum, valerian oil, basilici aetheroleum, bergamot oil, savory oil, bucco aetheroleum, camphor, cardamomi aetheroleum, cassia oil, chenopodium oil, chrysanthemum oil, cinae aetheroleum, citronella oil, lemon oil, citrus oil, costus oil, curcuma oil, carlina oil, elemi oil, tarragon oil, eucalyptus oil, fennel oil, pine needle oil, pine oil, filicis, aetheroleum, galbanum oil, gaultheriae aetheroleum, geranium oil, guaiac wood oil, hazelwort oil, iris oil, hypericum oil, calamus oil, camomile oil, fir needle oil, garlic oil, coriander oil, carraway oil, lauri aetheroleum, lavender oil, lemon grass oil, lovage oil, bay oil, lupuli strobuli aetheroleum, mace oil, marjoram oil, mandarine oil, melissa oil, menthol, millefolii aetheroleum, mint oil, clary oil, nutmeg oil, spikenard oil, clove oil, neroli oil, niaouli, olibanum oil, ononidis aetheroleum, opopranax oil, orange oil, oregano oil, orthosiphon oil, patchouli oil, parsley oil, petit-grain oil, peppermint oil, tansy oil, rosewood oil, rose oil, rosemary oil, rue oil, sabinae aetheroleum, saffron oil, sage oil, sandalwood oil, sassafras oil, celery oil, mustard oil, serphylli aetheroleum, immortelle oil, fir oil, teatree oil, terpentine oil, thyme oil, juniper oil, frankincense oil, hyssop oil, cedar wood oil, cinnamon oil, and cypress oil; and other oils such as, for example, fish oil; and any analogs, derivatives, copolymers and combinations thereof.

The molecular weights of the plasticizers can vary. In some embodiments, the molecular weights of the plasticizers range from about 10 Daltons to about 50,000 Daltons; from about 25 Daltons to about 25,000 Daltons; from about 50 Daltons to about 10,000 Daltons; from about 100 Daltons to about 5,000 Daltons; from about 200 Daltons to about 2500 Daltons; from about 400 Daltons to about 1250 Daltons; and any range therein. In other embodiments, the molecular weights of the plasticizers range from about 400 Daltons to about 4000 Daltons; from about 300 Daltons to about 3000 Daltons; from about 200 Daltons to about 2000 Daltons; from about 100 Daltons to about 1000 Daltons; from about 50 Daltons to about 5000 Daltons; and any range therein. The molecular weights are taught herein as a number average molecular weight.

The amount of plasticizer used in the teachings herein, can range from about 0.001% to about 70%; from about 0.01% to about 60%; from about 0.1% to about 50%; from about 0.1% to about 40%; from about 0.1% to about 30%; from about 0.1% to about 25%; from about 0.1% to about 20%; from about 0.1% to about 10%; from about 0.4% to about 40%; from about 0.6% to about 30%; from about 0.75% to about 25%; from about 1.0% to about 20%; and any range therein, as a weight percentage based on the total weight of the polymer and agent or combination of agents.

It should be appreciated that any one or any combination of the plasticizers described above can be used in the teachings herein. For example, the plasticizers can be combined to obtain the desired function. In some embodiments, a secondary plasticizer is combined with a primary plasticizer in an amount that ranges from about 0.001% to about 20%; from about 0.01% to about 15%; from about 0.05% to about 10%; from about 0.75% to about 7.5%; from about 1.0% to about 5%, or any range therein, as a weight percentage based on the total weight of the polymer any agent or combination of agents.

One embodiment applies gamma irradiation or electron beam (e-beam) sterilization. Other types of radio sterilization can be used.

In some embodiments, the drug-containing layer may be applied to a surface of a prosthesis, and the drug-reservoir layer may be applied on or over the drug layer. In some embodiments, the prosthesis can comprise a fitting for mechanically coupling to an adjacent tissue, such as calcified or soft tissue, for example, a bone CBD or TCH or intra-organ CBD or TCH. In some embodiments, the system may comprise an entirely resorbable construct, such as a capsule, a tablet, a pellet, a shaft, a rod, a sphere, disc, or a ring. In some embodiments, the resorbable construct may be configured for deployment in an anatomic environment such as the gastrointestinal tract, a synovial joint, a cardiovascular lumen, a cardiovascular chamber, a urinary lumen, a urinary chamber, a reproductive lumen, a reproductive chamber, a gynecological lumen, a gynecological chamber, an endocrine lumen, or an endocrine chamber.

In one example, a tubular drain system can be CBD or TCHed, leading from one of the ventricles of the brain to an abdominal position. One or more portions, or all, or the drain system may be coated and configured to promote endothelization/healing by substantially blocking elution of antiproliferative drugs, before controllably eluting drugs to prevent excessive fibrous cellular encapsulation and/or stenosis.

In another example, portions of a "venous" needle or "arterial" needle in an arteriovenous fistula may be coated and configured to promote endothelization/healing by substantially blocking elution of antiproliferative drugs, before controllably eluting drugs to prevent stenosis and/or excessive cellular encapsulation. Many transcutaneous port or cannulation device configurations may be so treated.

In another example, portions of pacemaker, defibrillator, or other CBD or TCHable device leads, such as a distal portion configured to engage a portion of the endocardial wall, may be coated and configured to promote endothelization/healing by substantially blocking elution of antiproliferative drugs, before controllably eluting drugs to prevent excessive cellular encapsulation.

In another example, portions of an intraocular lens prosthesis, such as the main body or legs of the prosthesis may be coated and configured to promote endothelization/healing by substantially blocking elution of antiproliferative drugs, before controllably eluting drugs to prevent excessive cellular encapsulation.

In another example, portions of a bile duct or other duct, tube, vessel, or lumen prosthesis may be coated and configured to promote endothelization/healing by substantially blocking elution of antiproliferative drugs, before controllably eluting drugs to prevent stenosis and/or excessive cellular encapsulation.

In another example, pellets or small prostheses used to treat tissue volumes such as those of a prostate gland may be coated and configured to promote endothelization/healing by substantially blocking elution of antiproliferative drugs, before controllably eluting drugs.

In another example, immunosuppressants and/or cytotoxics, such as taxol, can be delivered in such devices to aid in the treatment of tumors, such as prostate or other tumors. Pellets containing such drugs, for example, may be delivered through the urethra or by other surgical means.

An embodiment of the invention can be used where two or more segments of bone need to be aligned and require flexibility and changes of material properties based on temperature when device is placed.

An embodiment of the invention can help with broken bones, trauma, or other types of surgery but also building design or transportation design.

All references, patents, patent applications or other documents cited are hereby incorporated by reference herein in their entirety.

A natural feel is achieved through viscoelastic harmony of properties between the existing tissue and the CBD or TCH. This can be done by manipulating the viscous component of the CBD or TCH through flow properties by way of the particle size and particle size distribution ratios. The elastic component is intrinsic within the material tertiary structure (molecular weight and steric hindrance) and cross linking densities. The interpenetrating polymer network hydrogels have a number of desirable properties. These properties include high tensile strength with high water content, making the interpenetrating polymer network hydrogels excellent for use in dermal filling applications. Other advantages and features include: longevity without touch up, hypervolumic degradation, anatomic compliant and iso-osmotic controlled, among others.

The present invention has been described particularly in connection with a breast, butt, or body CBD or TCH, among others, but it will be obvious to those of skill in the art that the invention can have application to other parts of the body, such as the face, and generally to other soft tissue or bone. Accordingly, the invention is applicable to replacing missing or damaged soft tissue, structural tissue or bone, or for cosmetic tissue or bone replacement.

Although the present invention has been described in relation to particular embodiments thereof, many other variations and modifications and other uses will become apparent to those skilled in the art. It is preferred, therefore, that the present invention be limited not by the specific disclosure herein, but only by the appended claims. The other methods, used for characterization of the products according to one embodiment are described in the following examples which illustrate preferred embodiments of one embodiment without, however, being a limitation thereof. Variations and modifications can, of course, be made without departing from the spirit and scope of the invention.

What is claimed is:

1. A transdermal patch for treating pain in a human in need thereof consisting essentially of microneedles coupled to a reservoir, *cannabis* and insulin.

\* \* \* \* \*